United States Patent
Pedersen et al.

(10) Patent No.: US 7,618,432 B2
(45) Date of Patent: Nov. 17, 2009

(54) VALVULOPLASTY DEVICES AND METHODS

(75) Inventors: Wesley Pedersen, Minneapolis, MN (US); Robert A. Van Tassel, Excelsior, MN (US); Robert S. Schwartz, Rochester, MN (US); Gregory G. Brucker, Minneapolis, MN (US); Skott E. Greenhalgh, Glenside, PA (US)

(73) Assignee: InterValve, Inc., Eden Prairie, MN (US)

( * ) Notice: Subject to any disclaimer, the term of this patent is extended or adjusted under 35 U.S.C. 154(b) by 930 days.

(21) Appl. No.: 10/856,494

(22) Filed: May 27, 2004

(65) Prior Publication Data

US 2005/0090846 A1    Apr. 28, 2005

Related U.S. Application Data

(60) Provisional application No. 60/547,896, filed on Feb. 25, 2004, provisional application No. 60/488,635, filed on Jul. 18, 2003.

(51) Int. Cl.
*A61M 29/00* (2006.01)
*A61F 2/06* (2006.01)

(52) U.S. Cl. ..................................... 606/194; 623/1.11

(58) Field of Classification Search ................ 606/191, 606/194, 195, 198; 604/96.01
See application file for complete search history.

(56) References Cited

U.S. PATENT DOCUMENTS

| | | | |
|---|---|---|---|
| 4,327,736 A | 5/1982 | Inoue | |
| 4,630,609 A | 12/1986 | Chin | |
| 4,777,951 A | 10/1988 | Cribier et al. | |
| 4,787,388 A | 11/1988 | Hofmann | |
| 4,819,751 A | 4/1989 | Shimada et al. | |
| 4,878,495 A | 11/1989 | Grayzel | |
| 4,909,252 A | 3/1990 | Goldberger | |
| 4,927,412 A | 5/1990 | Menasche | |
| 4,986,830 A | 1/1991 | Owens et al. | |
| 5,037,392 A | 8/1991 | Hillstead | |
| 5,074,845 A | 12/1991 | Miraki et al. | |
| 5,250,070 A | 10/1993 | Parodi | |
| 5,295,995 A | 3/1994 | Kleiman | |
| 5,352,199 A | 10/1994 | Tower | |
| 5,443,446 A | 8/1995 | Shturman | |

(Continued)

FOREIGN PATENT DOCUMENTS

EP    0 344 530    12/1989

(Continued)

OTHER PUBLICATIONS

Eisenhauer et al., *Balloon Aortic Valvuloplasty Revisited: The Role of the Inoue Balloon and Transseptal Antegrade Approach*; Catheterization and Cardiovascular Interventions, Mar. 2, 2000, 484-491, vol. 50, Wiley-Liss, Inc., MA.

*Primary Examiner*—Vy Q Bui
(74) *Attorney, Agent, or Firm*—Inskeep IP Group, Inc.

(57) ABSTRACT

The present invention provides an aortic valvuloplasty catheter which, in one preferred embodiment, has a tapered distal balloon segment that anchors within the left ventricle outflow track of the patient's heart and a rounded proximal segment which conforms to the aortic sinuses forcing the valve leaflets open. In addition, this embodiment of the valvuloplasty catheter includes a fiber-based balloon membrane, a distal pigtail end hole catheter tip, and a catheter sheath.

13 Claims, 18 Drawing Sheets

U.S. PATENT DOCUMENTS

| | | |
|---|---|---|
| 5,470,313 A | 11/1995 | Crocker et al. |
| 5,545,209 A | 8/1996 | Roberts et al. |
| 5,549,551 A | 8/1996 | Peacock, III et al. |
| 5,653,690 A | 8/1997 | Booth et al. |
| 5,843,116 A | 12/1998 | Crocker et al. |
| 5,868,708 A | 2/1999 | Hart et al. |
| 5,908,448 A * | 6/1999 | Roberts et al. .............. 623/1.23 |
| 5,947,924 A | 9/1999 | Liprie |
| 5,961,536 A | 10/1999 | Mickley et al. |
| 6,267,747 B1 * | 7/2001 | Samson et al. ......... 604/103.07 |
| 6,296,660 B1 | 10/2001 | Roberts et al. |
| 6,344,045 B1 | 2/2002 | Lim et al. |
| 6,511,469 B2 | 1/2003 | Ackerman et al. |
| 6,537,247 B2 | 3/2003 | Shannon |
| 6,544,224 B1 | 4/2003 | Steese-Bradley |
| 6,562,056 B2 | 5/2003 | Jervis |
| 6,565,589 B1 | 5/2003 | Jervis et al. |
| 6,607,544 B1 | 8/2003 | Boucher et al. |
| 6,607,545 B2 | 8/2003 | Kammerer et al. |
| 6,626,861 B1 | 9/2003 | Hart et al. |
| 6,632,196 B1 | 10/2003 | Houser |
| 6,645,222 B1 | 11/2003 | Parodi et al. |
| 6,663,647 B2 | 12/2003 | Reiley et al. |
| 2001/0047163 A1 | 11/2001 | Samson et al. |

FOREIGN PATENT DOCUMENTS

| | | |
|---|---|---|
| EP | 0 351 734 | 1/1990 |
| EP | 0 419 291 | 3/1991 |
| EP | 0 669 143 | 8/1995 |
| EP | 0 829 271 | 3/1998 |
| EP | 1 062 966 | 12/2000 |
| EP | 1 352 671 | 10/2003 |
| EP | 1 352 672 | 10/2003 |
| WO | WO 89/02763 | 4/1989 |
| WO | WO 91/01773 | 2/1991 |
| WO | WO 95/23625 | 9/1995 |
| WO | WO 99/15223 | 4/1999 |

* cited by examiner

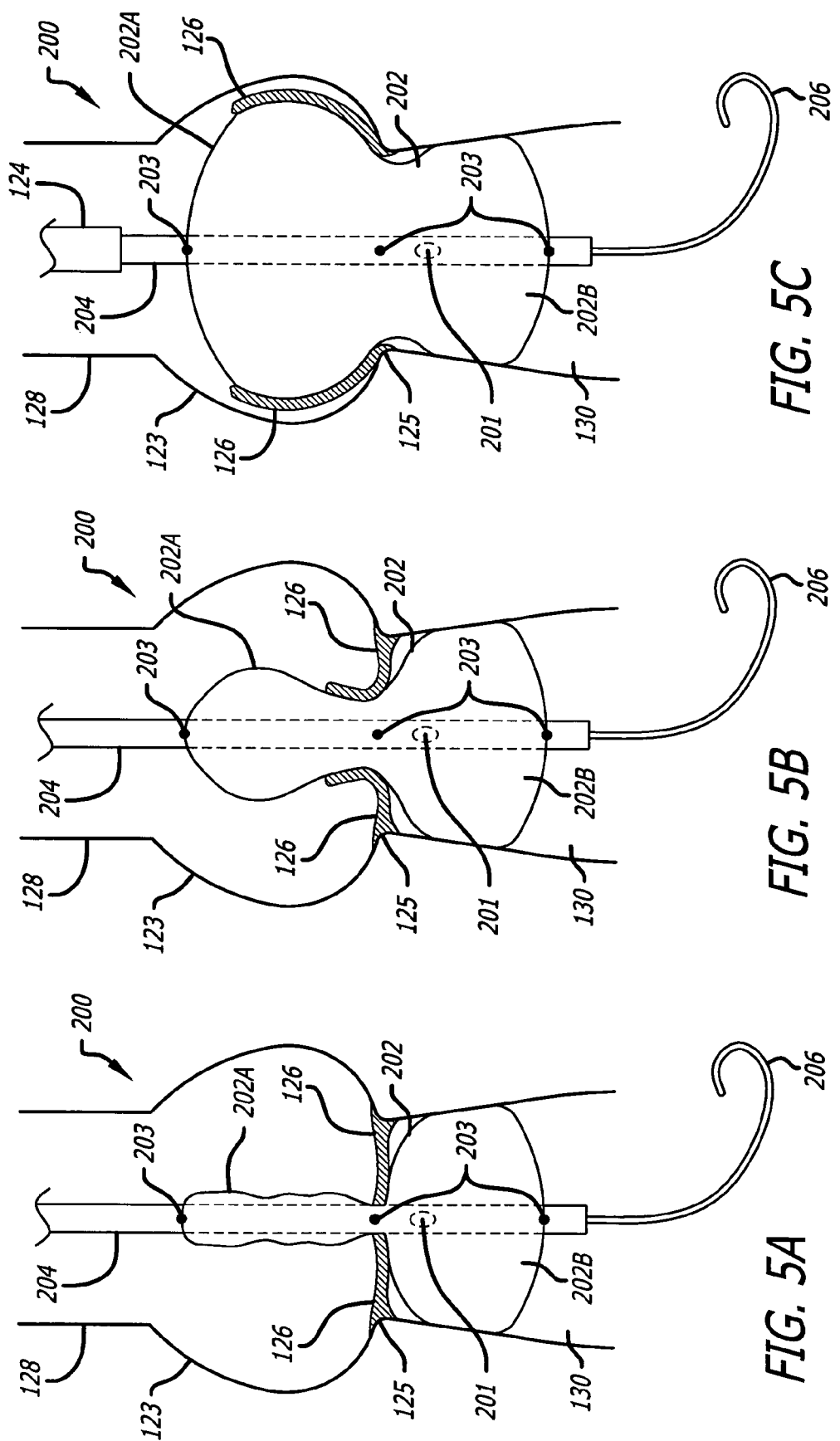

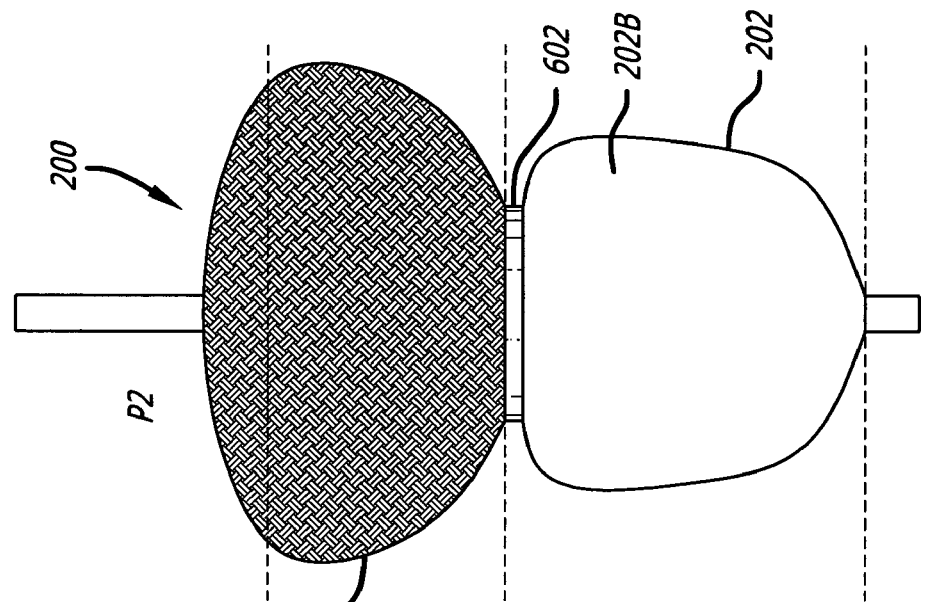
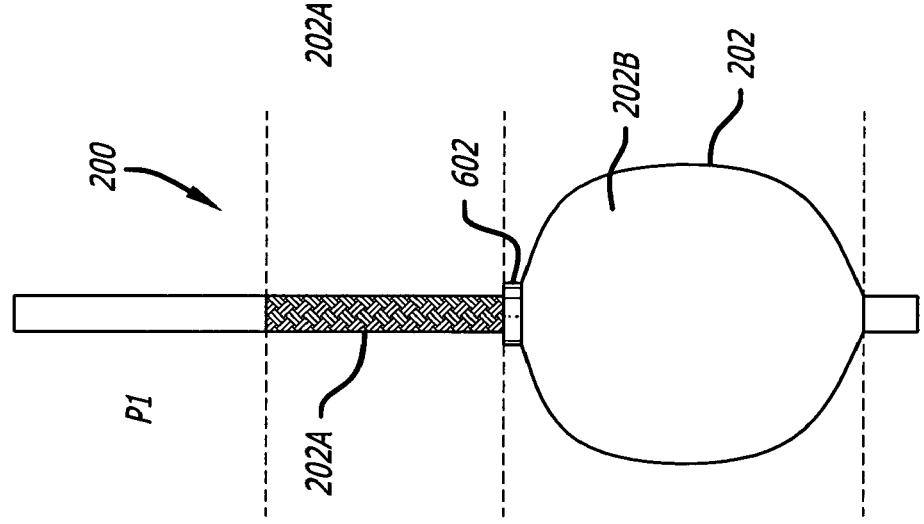
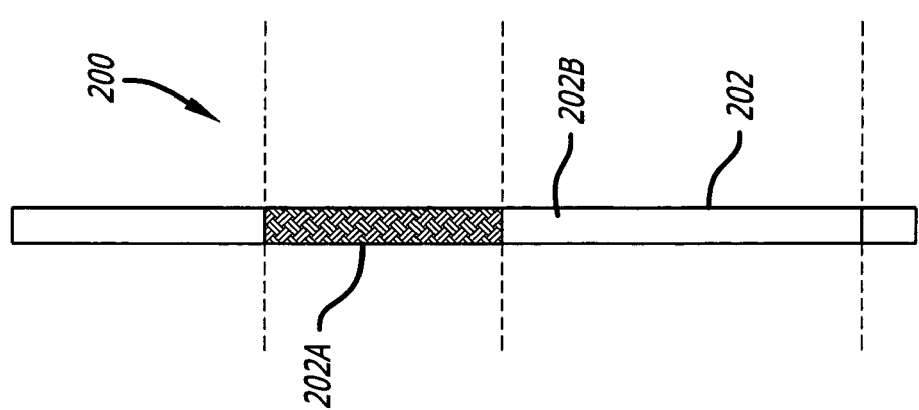
FIG. 5F
FIG. 5E
FIG. 5D

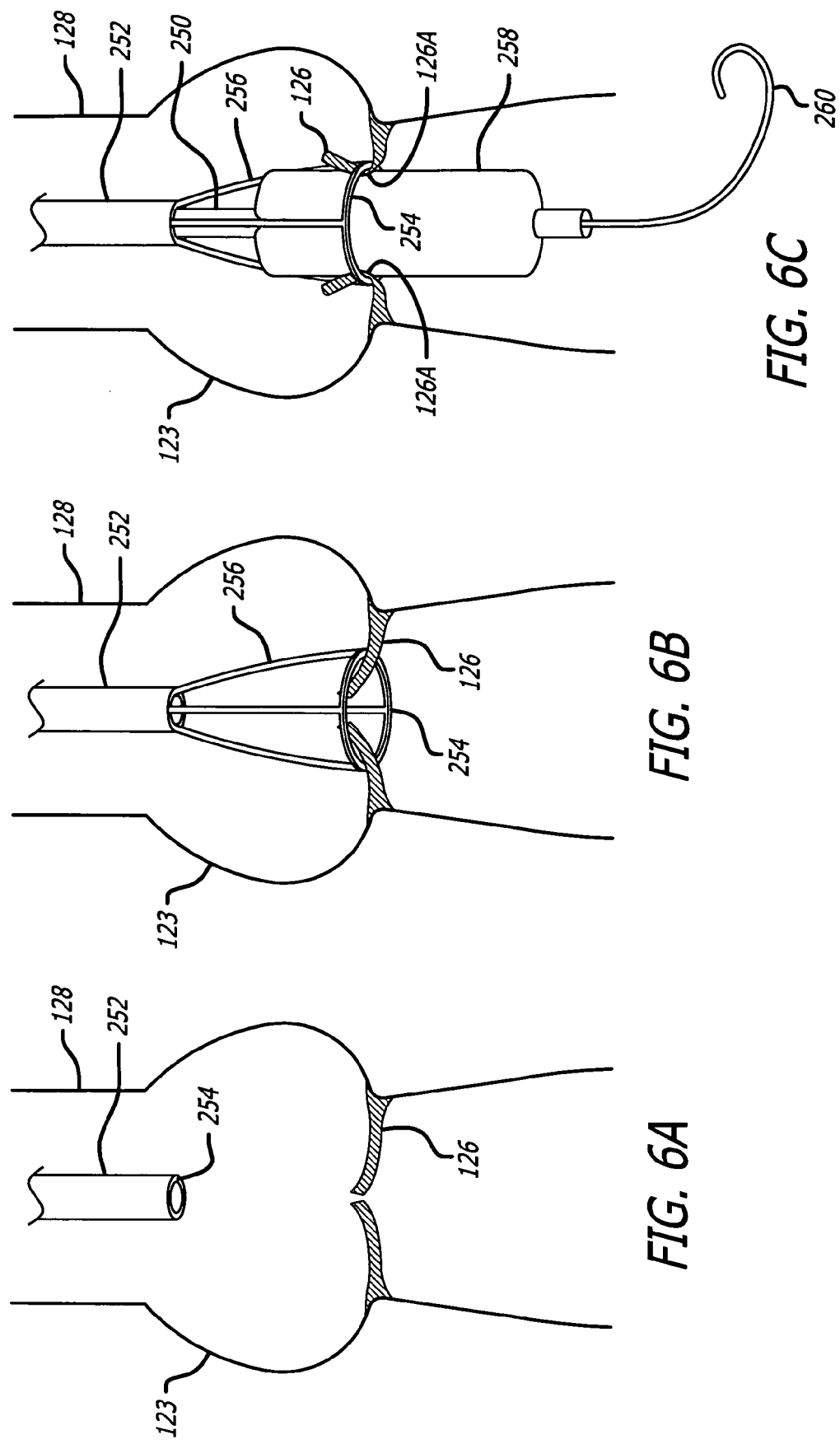

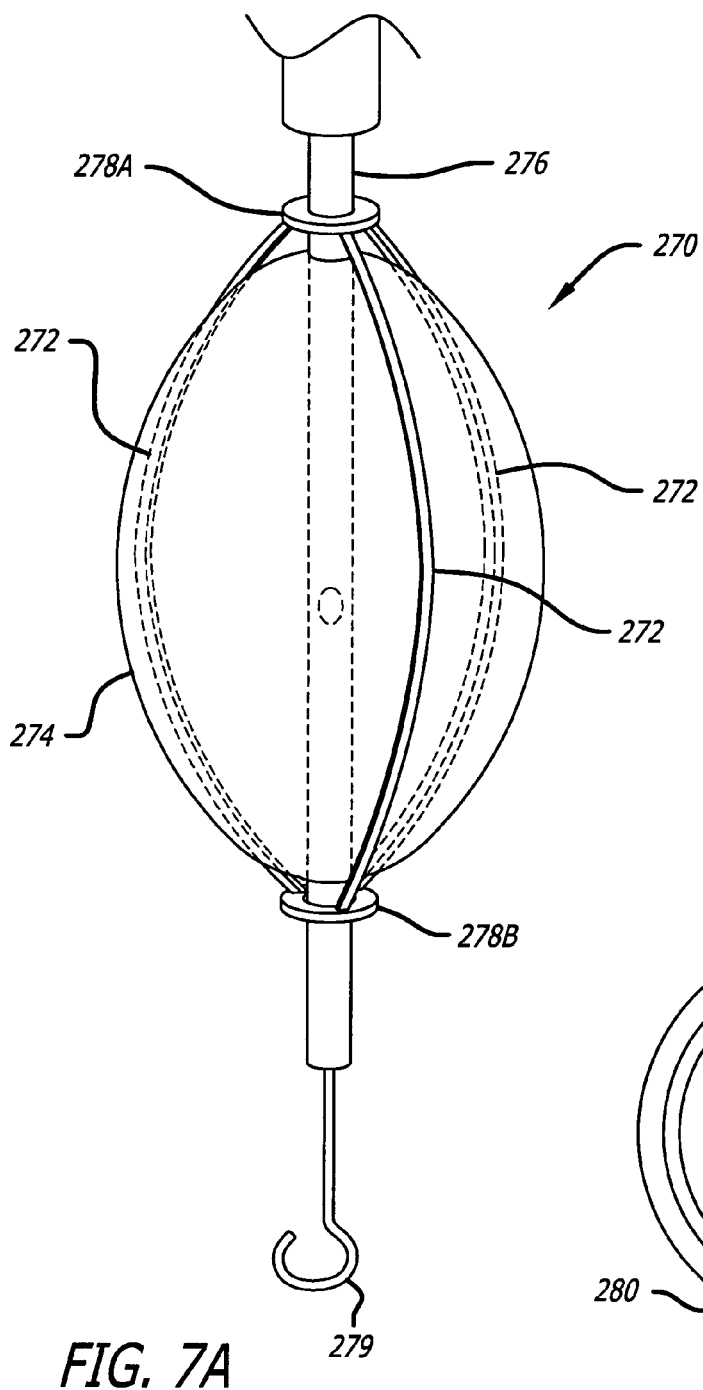
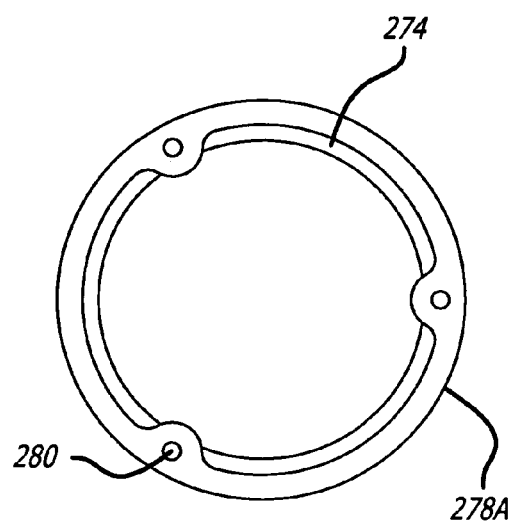
FIG. 7A
FIG. 7B

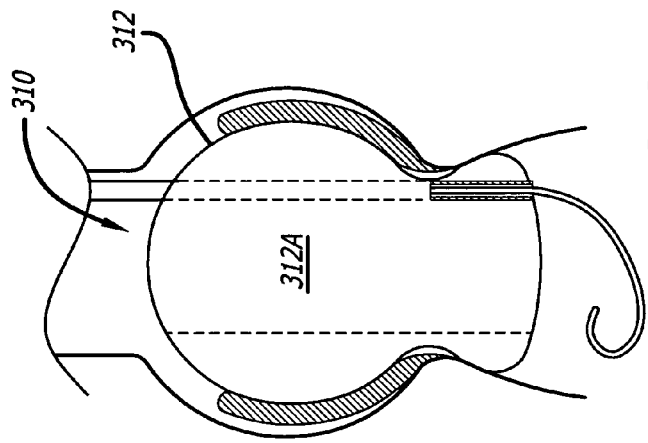
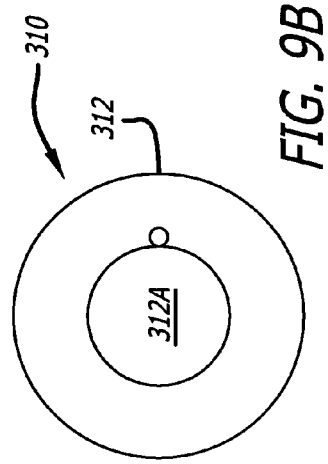
FIG. 9A
FIG. 9B
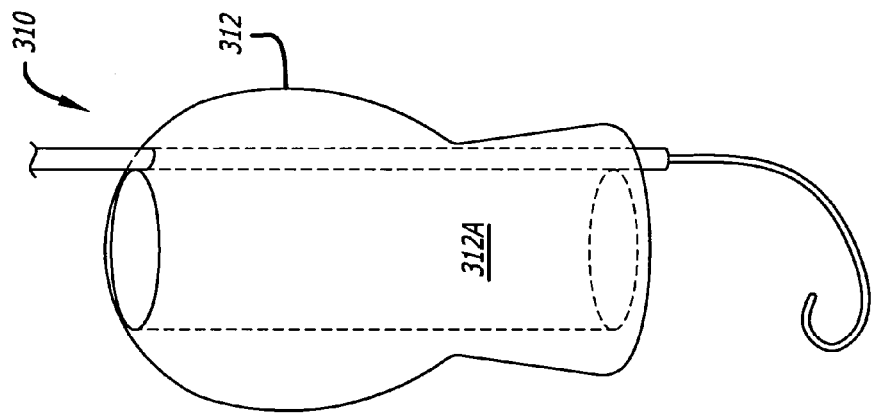
FIG. 9
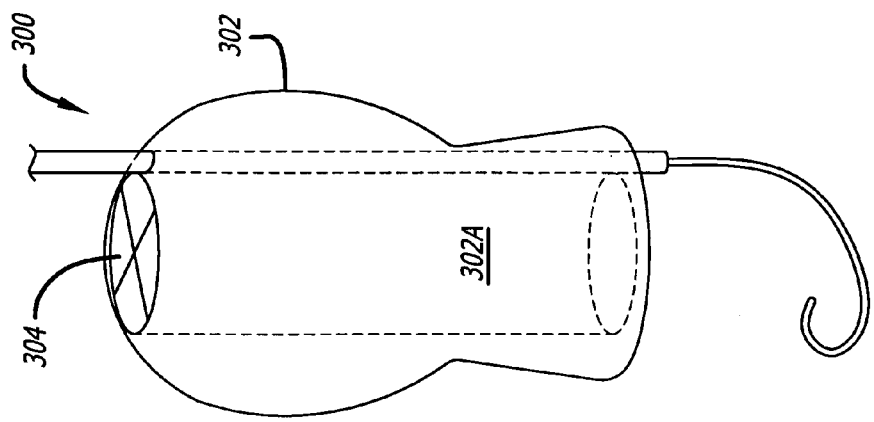
FIG. 8

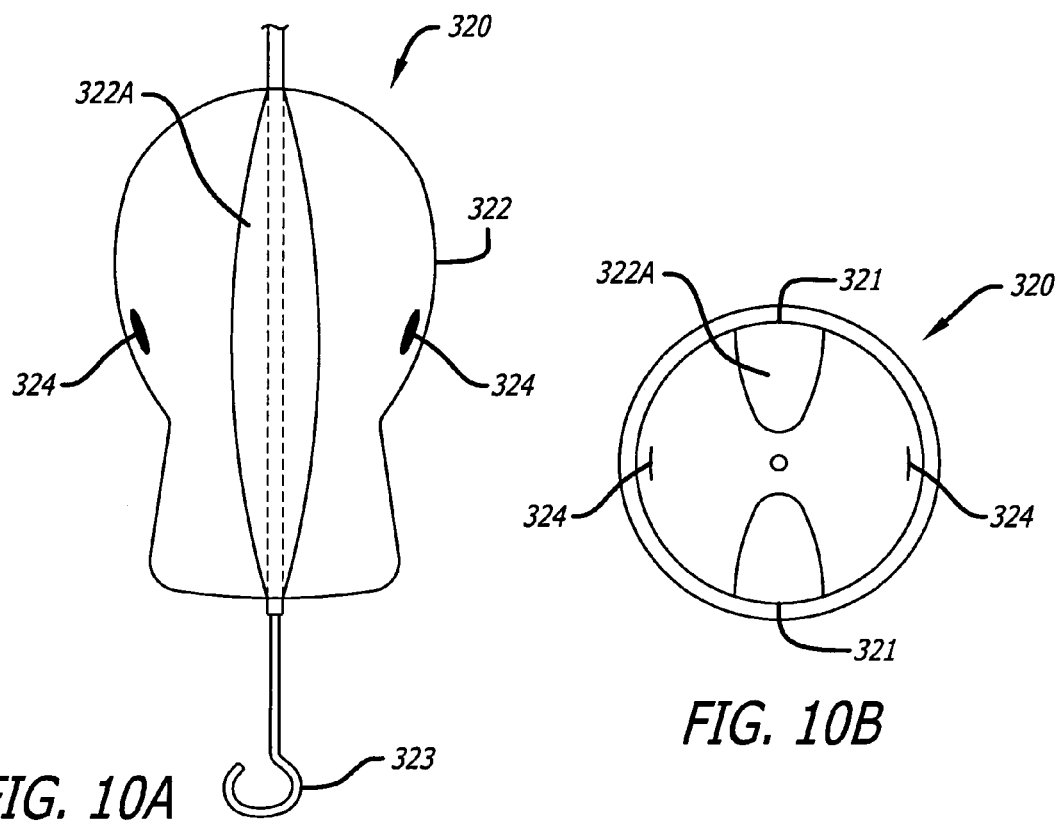
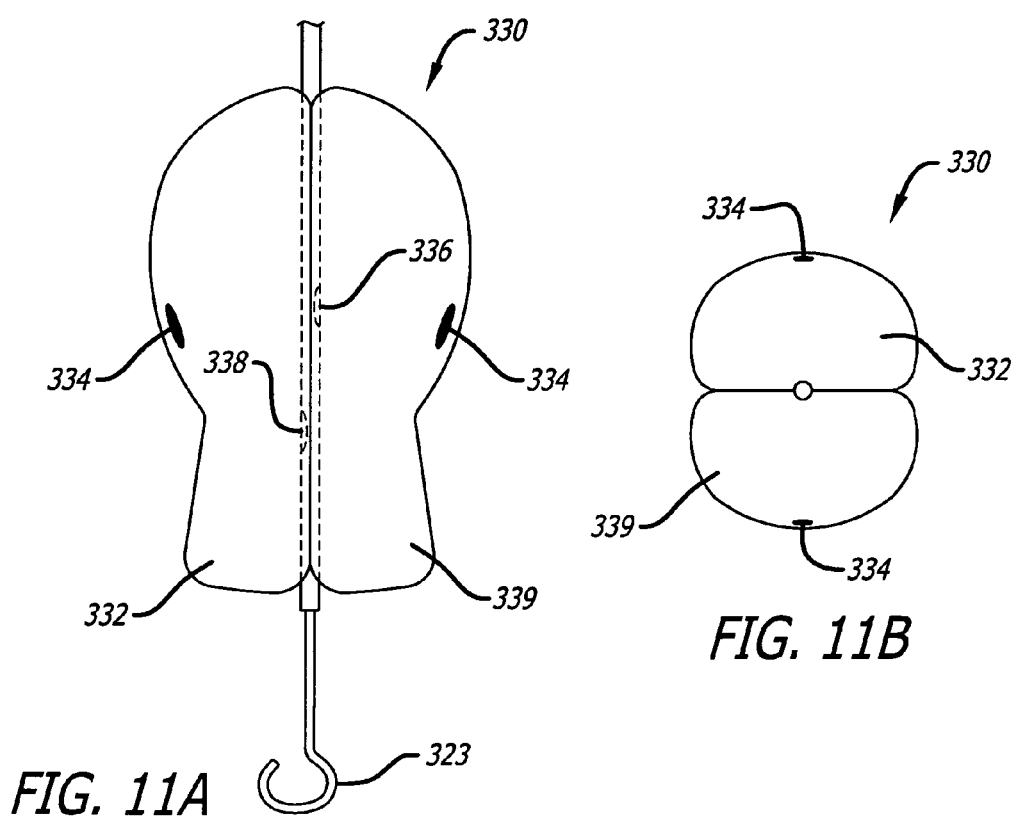

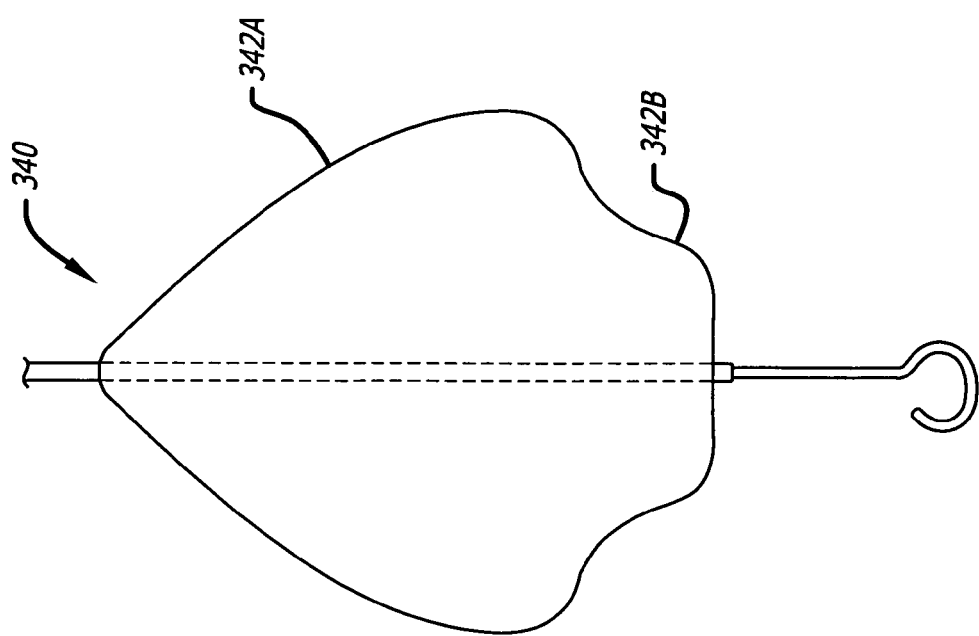
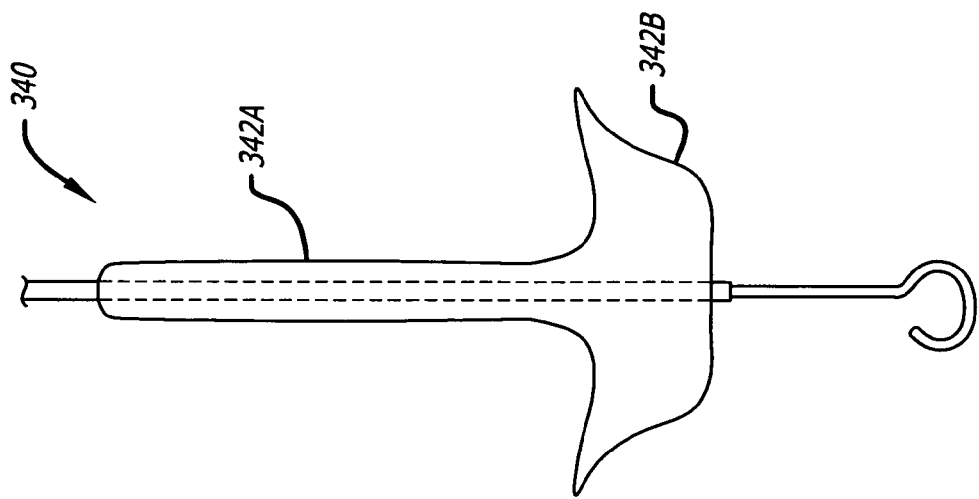
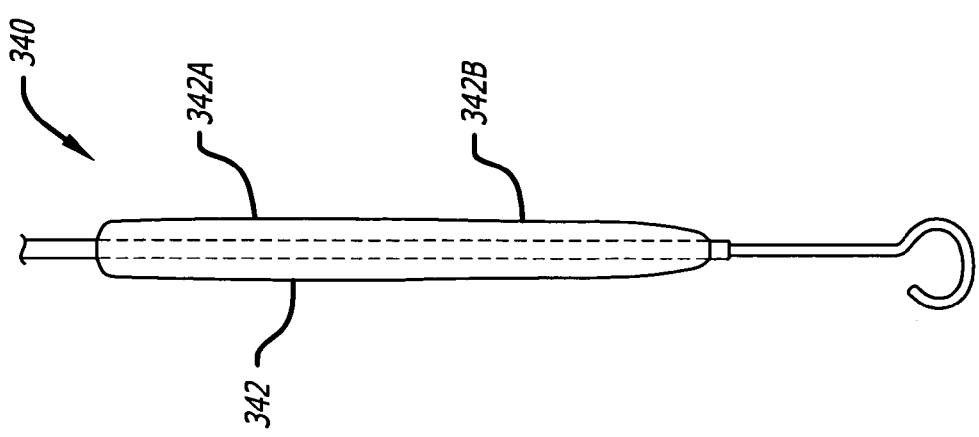
FIG. 12C
FIG. 12B
FIG. 12A

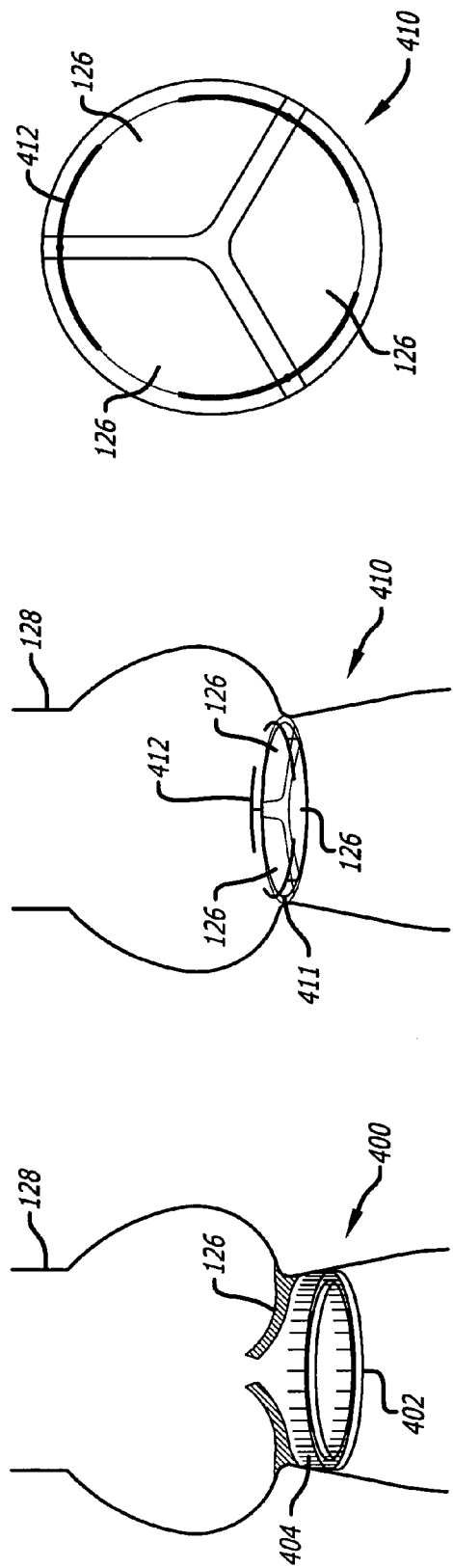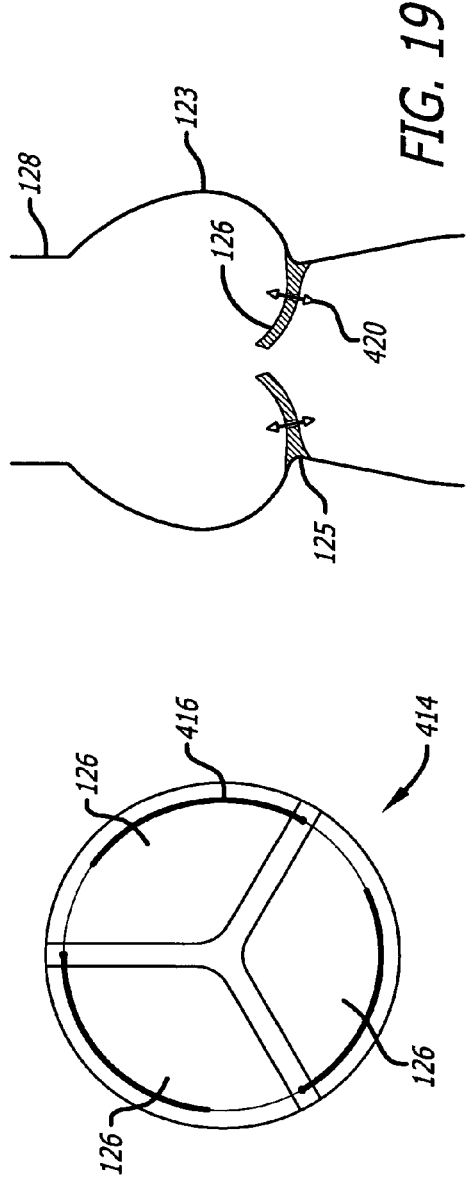

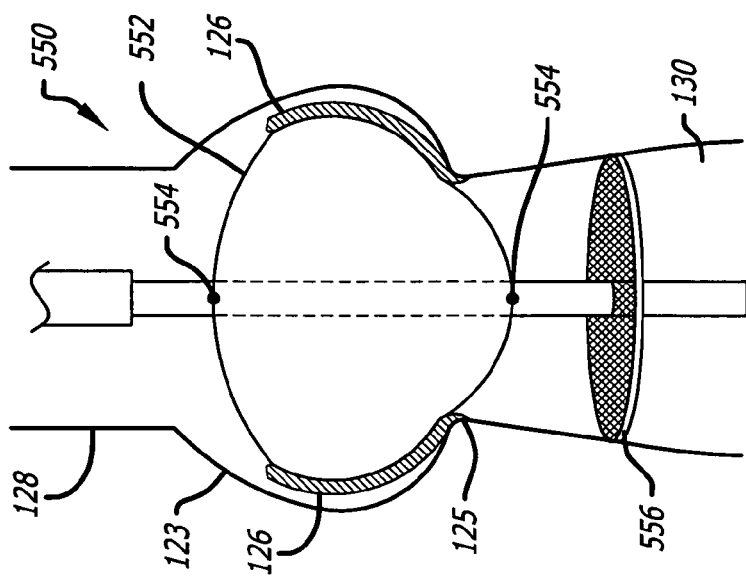
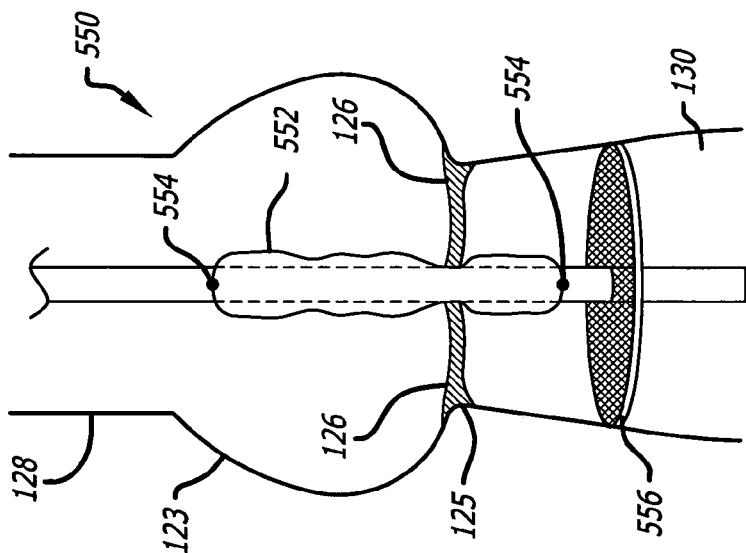
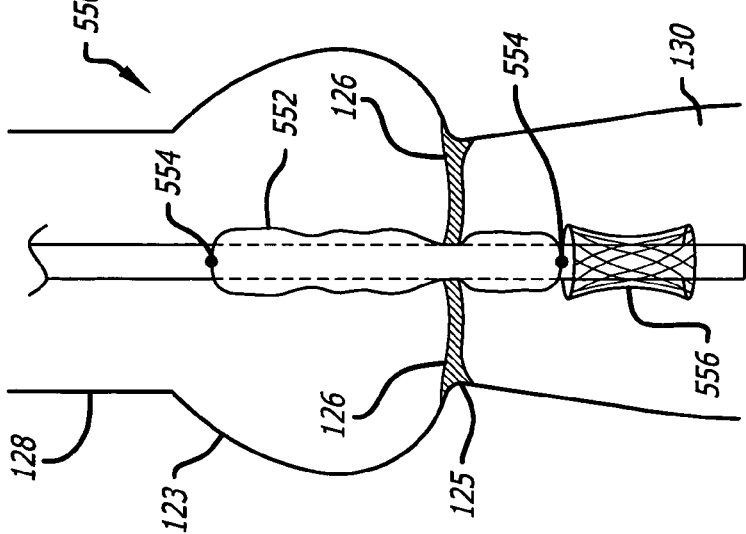

VALVULOPLASTY DEVICES AND METHODS

CROSS REFERENCE TO RELATED APPLICATIONS

This application claims the benefit of U.S. Provisional Application 60/488,635, entitled Enhanced Dilatation Catheter For Treatment Of Aortic Stenosis, filed Jul. 18, 2003 and U.S. Provisional Application 60/547,896 entitled Catheter For Treatment of Aortic Valves, filed Feb. 25, 2004, the entire contents of each being hereby incorporated by reference.

FIELD OF INVENTION

This invention relates to balloon catheters and other related mechanical devices for medical use. More particularly, this invention relates to balloon catheters with advanced anchoring and valvuloplasty capabilities. The invention also relates to controlling the expansion and force properties of a balloon in a balloon catheter through various means, including the reinforcement of the balloon through fibers located on the balloon.

BACKGROUND OF THE INVENTION

Calcific aortic stenosis is a common cause of acquired valvular heart disease with substantial morbidity and mortality. Its incidence increases exponentially in older patient populations. Fibrosis, degeneration and subsequent calcification are no longer believed to be passive or purely degenerative in nature, but in fact are predominantly active processes mediated by underlying cellular mechanisms. Over time, as fibrosis and calcification worsens, valve leaflets become increasingly rigid, restricting their ability to open. This in turn, then impedes the antegrade flow of blood through the heart resulting in several clinical syndromes including most significantly progressive heart failure. Other causes of deformed and stenotic aortic valvular lesions include rheumatic heart disease, as well as nonacquired (i.e. congenital) heart disease. Initial stages of stenotic valvular heart conditions are well tolerated by the patient, but when leaflet restriction becomes severe, drastic measures such as aortic valve replacement have commonly been required.

With the advent of catheter-based cardiovascular procedures, minimally invasive valvuloplasty techniques were developed to dilate stenosed valves, most commonly calcific aortic stenosis but also rheumatic and congenitally stenosed leaflets using catheter balloons. During this procedure, a catheter having a deflated balloon is percutaneously inserted into a vein or artery and advanced until the balloon is positioned within the heart valve needing treatment. The balloon is then inflated to dilate the diseased valve opening, disrupting the rigid sheets of calcium permitting enhanced leaflet mobility. Balloon dilation, depending on the disease process, may result not only in the development of numerous flexible hinge points within fibrosed and calcified leaflets but, in addition, separation of fused commissures can take place. After the leaflets have been dilated, the balloon is deflated and removed from the patient's cardiovascular system.

In many current instances, valvuloplasty is performed with polyethylene balloon catheters which can achieve relatively high pressures at a fixed diameter. Balloons made of non-distensible plastic materials are expanded using fluid pressure up to a certain diameter after which, increases in fluid pressure within the balloon produce very little change in balloon diameter. These balloons can achieve high pressures for an effective therapy, but inherent to this plastic material are several limitations. The profile of these balloons can be somewhat reduced by prefolding during the manufacturing process. However, once inflated, the folded balloon segments are expanded within the vascular system and when deflated for removal, do not return to their compact, prefolded state but to a flattened state with a much larger profile. Withdrawal of these balloons therefore requires larger vascular introductory sheaths and thereby increases the risk of trauma to the vessels, resulting in compromised blood flow to an extremity or post operative bleeding. Additionally, non-distensible balloons also have thick cones—transitions from the cylindrical diameter to the catheter shaft diameter. These regions of the balloon make the catheter stiff increasing the risk of vascular trauma and making it difficult to advance through tortuous peripheral arterial anatomy.

Since the radial dimensions of the catheter balloon must greatly increase when inflated to achieve aortic valve dilation, a highly elastic material such as latex can be used, but with significant limitations. Distensible balloons use these elastic materials and generally have excellent initial profiles and improved flexibility for introduction and travel through the vascular system. In addition, they possess good deflated profiles for removal from the vascular system. However, elastic materials such as this continue to expand in diameter as pressure increases and therefore have no inherent limit on maximal diameter as with non-distensible balloons. Thus, distensible balloons can be unsafe for such a purpose as valvuloplasty, as the elastic limit can easily be exceeded when the balloon is fully inflated, potentially causing the balloon to rupture within the patient. Additionally, the balloon diameters can become too large for the valve being dilated causing rupture and tearing of both the valve and its adjacent structures.

In addition, prior art catheter balloons have been associated with mechanical injury to the cardiac chambers, especially near the ventricular apex, due to the forceful longitudinal movement of the inflated balloon across the valve and within the cardiac chamber as the heart beats. Blood, and the vascular wall surface, are inherently slippery against common catheter balloons further increasing the risk of significant balloon migration. As inflation fluid (contrast media) is introduced, the catheter balloon enlarges and eventually assumes a cylindrical or ovoid shape. This creates a tendency for the balloon to suddenly and uncontrollably pop in and out of the valve site and migrate deep into the left ventricle. In some situations, this sudden balloon movement following inflation has not only made it difficult to position accurately within the valve leaflets but again has led to damage and even catastrophic puncturing of the left ventricle.

Further, typical catheter balloon shapes tend to completely obstruct the flow of blood through the heart while inflated. Without perfusion through or around the catheter, the catheter balloon inflation time is limited to a few seconds before risking complications due to profound hypotension.

A further disadvantage of prior art valvuloplasty balloons is their frequent failure to restore adequate flexibility to the aortic valve leaflets. That is, mere dilation with these previous balloon designs may not be enough to adequately open the severely fibrosed and calcified leaflets. The prior art balloon catheters are cylindrical in shape when fully inflated and thus have their maximal inflated diameter limited by the narrower sinotubular ridge and valve annulus at the proximal and distal margins of the aortic root sinuses. Efforts to expand beyond these limits for enhanced valve opening can result in tearing of the aortic valve annulus, catastrophic aortic insufficiency or rupture of the aortic root. In addition, traditional balloon catheter methods generally result in eventual restenosis of the aortic valve leaflets, negating some or all of the regained flexibility.

Examples of some of these prior art catheter designs, as well as other related catheter designs are discussed and disclosed in the following U.S. Pat. Nos. 4,327,736; 4,777,951; 4,787,388; 4,878,495; 4,819,751; 4,909,252; 4,986,830; 5,352,199; and 5,947,924.

What is needed is a balloon valvuloplasty catheter that overcomes all of the these disadvantages of the prior art. Indeed, what is needed is an invention that not only overcomes the disadvantages of the prior art in treating calcific aortic stenosis but also aortic stenosis resulting from congenitally abnormal valves and/or rheumatically injured valves.

Of particular need is a balloon configuration that has expansion characteristics that not only stabilize the valvuloplasty catheter at a desired location but that also provides the necessary a-traumatic expansion force to successfully perform the valvuloplasty. Moreover, it is desired to meet this need either with a single reinforced balloon configuration or a dual balloon configuration.

OBJECTS AND SUMMARY OF THE INVENTION

It is an object of the present invention to provide a balloon catheter that overcomes the shortcomings of the prior art.

It is a further object of the present invention to provide a catheter that can anchor itself so as to create a stable catheter position during valvuloplasty.

It is an object of the present invention to provide a tapered distal balloon catheter segment which is better able to anchor itself within the left ventricular outflow tract. Anchoring to create stable catheter positions for valvuloplasty can also be accomplished by other novel embodiments introduced in this patent application.

It is a further object of the present invention to provide a balloon catheter segment that conforms more accurately to the valve annular ring to prevent over stretching, mechanical trauma, or even tearing of this supporting structure.

It is yet a further object of the present invention to provide a rounded proximal balloon catheter segment that conforms to the shape of the aortic root to improve leaflet opening by creating broader and more effective hinge points on the aortic valve leaflets.

It is yet a further object of the present invention to provide a balloon catheter which allows antegrade (forward) perfusion of blood.

It is a further object of the present invention to overcome the disadvantages of the prior art.

It is a further object of the present invention to provide a drug delivery device for providing local anti-restenotic therapies and therapies to result in stenosis regression.

The present invention achieves these objects by providing an aortic valvuloplasty catheter which, in one preferred embodiment, has a tapered distal balloon segment that anchors within the left ventricle outflow track of the a patient's heart and a more proximal rounded segment to broadly dilate the aortic valve leaflets into the aortic root sinuses. In addition, this embodiment of the valvuloplasty catheter may include a fiber-based balloon membrane to aid in achieving a lower profile, higher pressure balloon with a specific geometric shape. In addition, this embodiment may be configured to permit distal perfusion while the balloon is inflated. It may have a pigtail distal tip to minimize any likelihood of intracardiac trauma. The entire catheter may be advanced through an elongated sheath to assure greater stability and permit measurement of central aortic pressures.

BRIEF DESCRIPTION OF THE DRAWINGS

FIGS. 5A-5C illustrate side views of a single balloon valvuloplasty catheter according to the present invention;

FIGS. 5D-5L illustrate side view of a single balloon valvuloplasty catheter using various fiber reinforced balloon characteristics in accordance with the present invention;

FIGS. 6A-6C illustrate side views of a ring and balloon catheter according to the present invention;

FIG. 7A illustrates a side view of a longitudinal wire catheter according to the present invention;

FIG. 7B illustrates a top view of a wire mounting ring of the longitudinal wire catheter of FIG. 7A;

FIG. 8 illustrates a side view of a center channel catheter according to the present invention;

FIG. 9 illustrates a side view of a center channel catheter according to the present invention;

FIGS. 9A-9B illustrates a side view and a top view of a center channel catheter according to the present invention;

FIG. 10A illustrates a side view of a valvuloplasty perfusion catheter according to the present invention;

FIG. 10B illustrates a bottom view of the valvuloplasty perfusion catheter of FIG. 10A;

FIG. 11A illustrates a side view of a dual balloon valvuloplasty catheter according to the present invention;

FIG. 11B illustrates a top view of the dual balloon valvuloplasty catheter of FIG. 11A;

FIGS. 12A-12C illustrate side views of an valvuloplasty catheter according to the present invention;

FIG. 16 illustrates a side view of a drug eluting device according to the present invention;

FIG. 17A illustrates a side view of a drug eluting device according to the present invention;

FIG. 17B illustrates a top view of the drug eluting device according in FIG. 17A;

FIG. 18 illustrates a top view of a drug eluting device according to the present invention;

FIG. 19 illustrates a side view of a drug eluting device according to the present invention;

FIGS. 23A-23C illustrate a side view of a mesh anchoring valvuloplasty catheter according to the present invention.

DETAILED DESCRIPTION OF THE INVENTION

During a typical valvuloplasty procedure, a balloon catheter is inserted percutaneously within a patient's vessel and advanced to a stenotic valve, for example, the aortic valve which is contiguous with the left ventricle of the heart. Once in a desired position within a valve, the catheter balloon is inflated with liquid contrast media, expanding the diameter of the balloon and forcing the valve leaflets open. By forcing the valve open for a brief time, the leaflets are able to regain at least a portion of their original flexibility, allowing for more normal cardiovascular function.

Aortic Valvuloplasty Catheter

Figure 1:
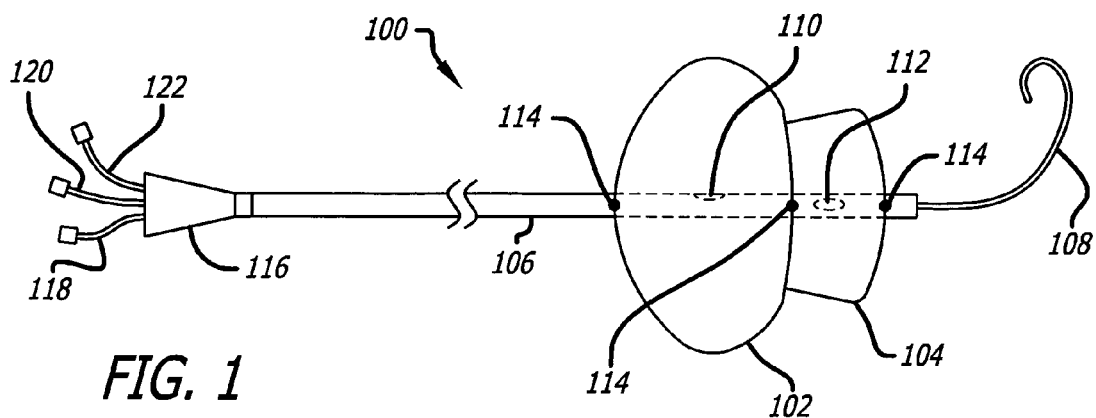
FIG. 1 illustrates a side view of an valvuloplasty catheter according to the present invention.
Figure 2A:
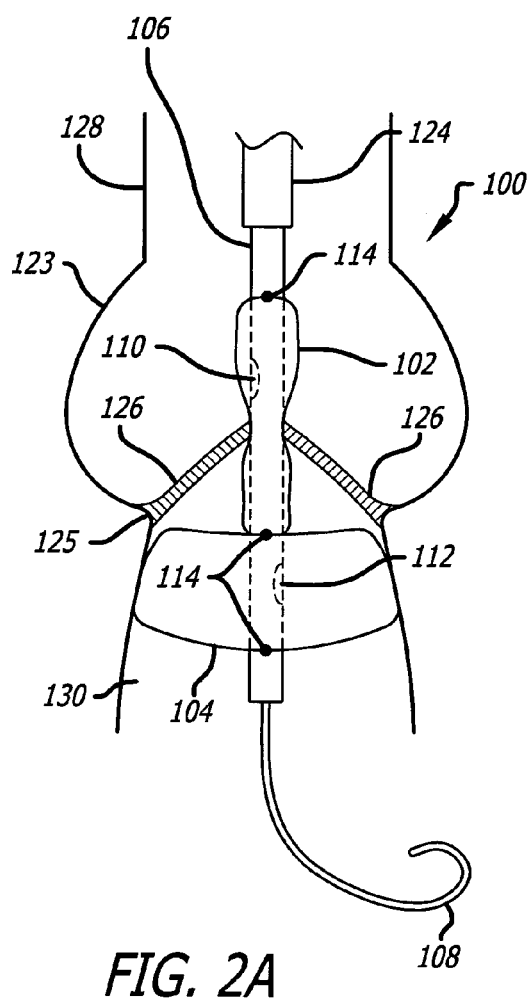
FIGS. 2A-2B illustrate a side view of the valvuloplasty catheter of FIG. 1.
Figure 2B:
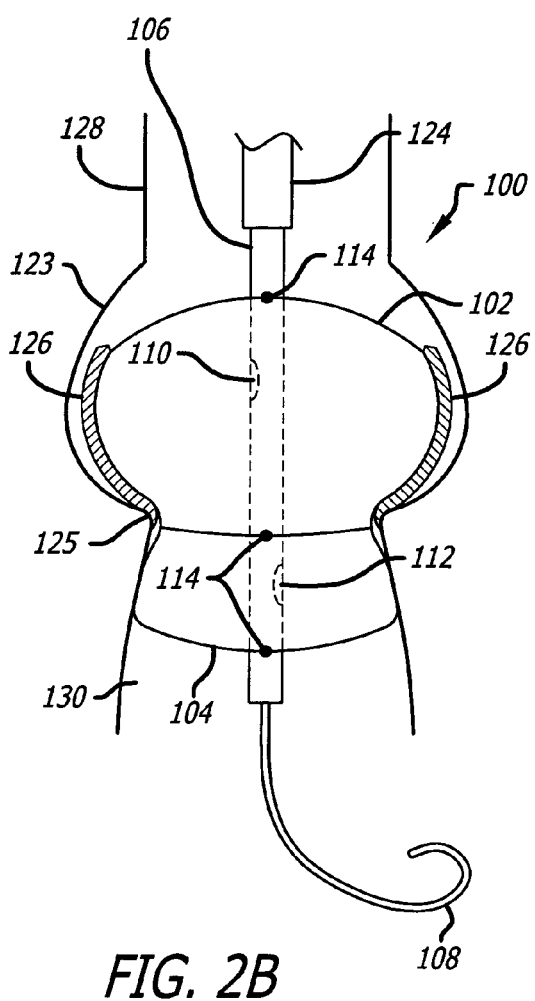

Turning to FIGS. 1, 2A, and 2B, a preferred embodiment of an aortic valvuloplasty catheter 100 is illustrated in accordance with the present invention, having an elongated catheter shaft 106 with a proximal, aortic sinus dilatation balloon 102 and a distal LVOT anchoring balloon 104 at the distal end of the catheter shaft 106. The distal anchoring balloon 104 provides anchoring support to the valvuloplasty catheter 100 by expanding within the left ventricular outflow tract 130 (LVOT), thus allowing the aortic sinus balloon 102 to maintain a desired position to expand against the aortic valve leaflets 126.

The catheter shaft 106 has multiple lumens (not shown) positioned axially within the catheter shaft 106 body, similar to those used for balloon angioplasty catheters. Each of the lumens opens at a proximal end of the catheter shaft 106, within the control hub 116, and terminates at varying points near the distal end of the catheter shaft 106, such as at a proximal aortic sinus balloon port 110 or a distal anchoring balloon port 112. Typically, the catheter shaft 106 has at least 3 lumens: a lumen for a guide wire 118, a lumen to communicate an inflation media to the aortic sinus balloon port 110, and a lumen to communicate an inflation media to the anchoring balloon port 112. Note that connecting fittings 120 and 122 can be seen in FIG. 1, which connect the two inflation lumens to external media supplies (not shown). Additional lumens for pressure measurement could be added to this catheter for simultaneous aortic and left ventricular pressures to derive aortic valve gradients pre and post valvuloplasty.

Additionally, radiopaque markers 114 are positioned at various locations on the catheter shaft 106, to mark, for example, the proximal and distal boundaries of the aortic sinus balloon 102 and the distal anchoring balloon 104. As such, the radiopaque markers 114 serve as visual guides during a valvuloplasty procedure to further assist positioning the enhanced aortic valvuloplasty catheter 100 of the present invention in a desired position within a patient's vascular system.

An angulated pigtail 108 is located at the distal end of catheter shaft 106 to prevent mechanical damage to the patient while the enhanced valvuloplasty catheter 100 is operated. The angulated pigtail 108 has a single hole (not shown) at its immediate distal end for passage of a guide wire and pressure measurement after the guide wire is removed. The single end hole design provides a more accurate pressure measurement when the balloon segments are retracted proximal to the aortic valve, leaving just the pigtail within the left ventricle. In comparison, a pigtail 108 with multiple side holes disposed along the length of the pigtail section can leave some of the holes proximal as well as distal to the valve, leading to inaccurate valve gradient measurements. It should be noted, however, that multiple side holes can be included in the angulated pigtail 108 for additional uses, such as radiopaque dye injections, or other purposes.

The distal anchoring balloon 104 is located at the distal end of catheter shaft 106, near angulated pigtail 108. The distal anchoring balloon 104 inflates with media communicated by anchoring balloon port 112, so as to press against the structure of the LVOT, fixing the longitudinal position of the aortic valvuloplasty catheter 100. Preferably, the cross sectional surface contour of the distal anchoring balloon 104 does not engage the LVOT throughout its entire circumference. This will permit perfusion around the distal anchoring balloon 104. For example, the distal anchoring balloon 104 may have a cross sectional shape of a star, spiral, or donut, of which additional details and examples are discussed in greater detail below. However, a distal anchoring balloon 104 that engages the entire circumference of the LVOT may be used so long as it is operated by quick inflation followed by quick deflation.

Prior art catheter balloons have been associated with mechanical injury to the heart, especially near the ventricular apex, due to the strong tendency for the inflated balloon to abruptly migrate back and forth across the aortic valve, darting in and out of the left ventricle due to phasic blood flow. Accordingly, the distal anchoring balloon 104 of the catheter 100 of the present invention preferably has a reverse taper distally where it would be larger in diameter. In this manner, the distal anchoring balloon 104 more closely conforms to the anatomical structure of the LVOT, preventing abrupt back and forth movement. It should be noted that the distal LVOT anchoring balloon 104 can be shaped to many different forms, who's purpose it is again to more tightly engage the LVOT for longitudinal fixation. An example includes an hour glass configuration to accommodate the hypertrophic, i.e. proximal, left ventricle septal bulge seen in many patients. A more adhesive balloon surface can be created by an external balloon fiber or other implants to prevent balloon slippage.

Preferably, the distal anchoring balloon 104 functions under low inflation pressure, for example less than about 3 atm. The distal anchoring balloon 104 is sized to engage the LVOT of a patient, having the preferable exemplary dimensions of about 15-20 mm in length, 24-28 mm in diameter for the distal end and 20-24 mm in diameter for the proximal end. However, since the size and shape of a LVOT may vary from patient to patient, the final distal anchoring balloon 104 size and shape may be selected to more closely conform to each LVOT.

The aortic sinus balloon 102 is located proximal to the distal anchoring balloon, having a sinus balloon port 110 to communicate media for inflating the aortic sinus balloon 102 against the valve leaflets 126. When inflated, the aortic sinus balloon 102 preferably conforms to the rounded shape of the aortic sinuses (as best seen in FIG. 2B), enabling the leaflets 126 to be opened as broadly as possible. This rounded proximal segment 192 would in fact permit hyperextension of the valve leaflets 126 into the aortic sinuses 123, yielding greater valve leaflet opening and consequently greater reduction in aortic valve gradient. It preferably is distensible through a wide range of predetermined diameters to take advantage of the range of diameters seen for the aortic sinuses in various patients. For example, the inflated aortic sinus balloon 102 may preferably be capable of achieving a balloon diameter of about 24 mm at about 4 ATMs of pressure and about 28 mm at 6 ATMs of pressure. Alternately, the aortic sinus balloon 102 can be primarily volume driven so that the balloon will achieve a range of diameters determined by the volume of media instilled. Preferably, the aortic sinus balloon 102 is about 18 mm in length, with a maximal diameter of about 24-30 mm.

Both the aortic sinus balloon 102 and the distal anchoring balloon 104 may be composed of a semi-elastic plastic. However, as higher pressures are utilized, especially for the aortic sinus balloon 102, the balloon membrane typically must substantially increase in thickness to guard against rupture of the balloon 102. Furthermore, the resultant need for a larger vascular entry sheath results in the inherent risk for percutaneous vascular injury. In this regard, fiber-based membranes are preferably used for both balloons 102 and 104 to increase the balloon membrane strength without the need to substantially increase thickness. The fabric reinforced balloon is also capable of allowing the formation of a specified geometric shape to the expanded balloon. Examples of such fiber based balloon membranes can be seen in the currently pending and commonly owned U.S. patent application Ser. No. 09/974,220, entitled Material Useable For Medical Balloons And Catheters, filed Oct. 9, 2001, the contents of which are herein incorporated by reference.

Figure 3:
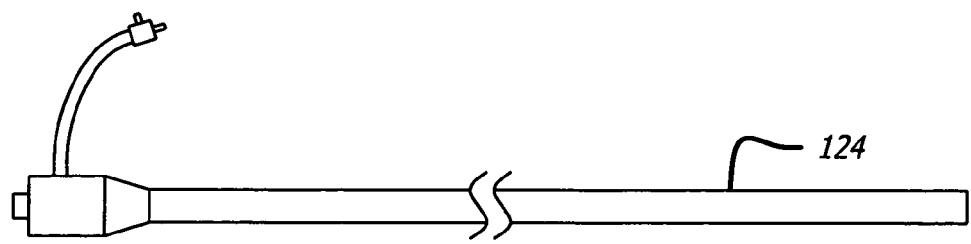
FIG. 3 illustrates a side view of a catheter sheath according to the present invention.

As seen in FIGS. 2A-3, an elongated sheath 124 may be used to introduce the valvuloplasty catheter 100 and assist in stabilizing it across the aortic valve during inflation, by preventing back and forth motion. Additionally, the sheath 124 can be used to measure the central aortic pressure which is useful for perioperatively monitoring and in determining the aortic valve pressure gradient following valve dilation. The sheath 124 may be used with the present preferred embodiment or any other of the subsequent embodiments described within this application.

In operation, the aortic valvuloplasty catheter 100 of the present invention is introduced through the femoral or brachial artery using a Seldinger technique to place a vascular sheath introducer in the peripheral vessel. After placement of a guidewire (not shown) across the aortic valve, the aortic valvuloplasty catheter 100 of the present invention is advanced retrograde over the guidewire such that the pigtail 108 is positioned in the left ventricle. Next, the distal anchoring balloon 104 is positioned using fluoroscopy within the LVOT 130, just underneath the valve annulus 125. The distal anchoring balloon 104 is inflated with fluid, e.g., contrast media, which is communicated through anchoring balloon inflation port 112, best seen in FIG. 2A. The distal anchoring balloon 104 expands in diameter as contrast media is added, allowing the distal anchoring balloon 104 to engage and press against the walls of the LVOT 130, thus longitudinally securing the position of the enhanced aortic valvuloplasty catheter 100. Once the distal anchoring balloon 104 is anchored securely within the LVOT 130, the aortic sinus balloon 102 is inflated, as seen in FIG. 2B, hyper-extending the valve leaflets 126 into the rounded aortic sinuses 123. In this regard, it may be necessary to inflate the aortic sinus balloon 102 at several different diameters to achieve the desired valve leaflet 126 flexibility and therefore the desired pressure gradient reduction. To ensure these goals have been achieved, the pressure gradient is measured using the distal guidewire lumen after the balloons 102, and 104 are withdrawn proximal to the aortic valve, leaving the pigtail 108 within the LVOT distal to the valve leaflets 126. A lumen within the sheath 124 may then be connected to a pressure transducer (not shown) at the proximal end of the sheath 124. Simultaneous central aortic and left ventricle pressure can then be measured to derive the valve gradient.

Microporous Filter Basket

Figure 4:
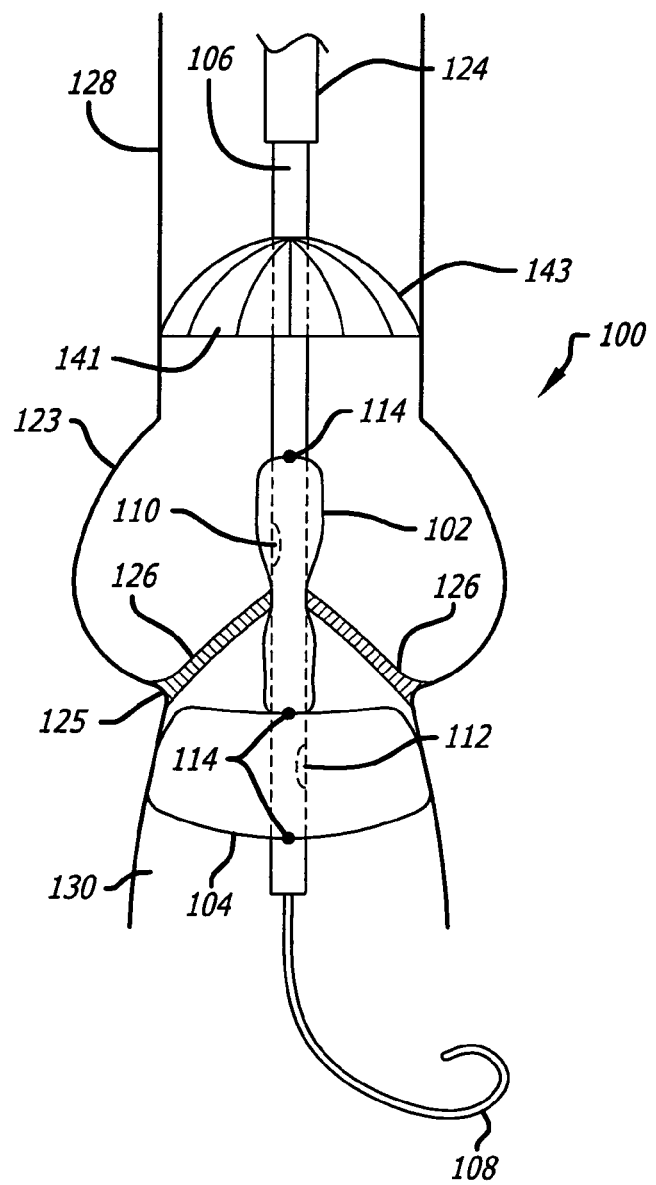
FIG. 4 illustrates a side view of a valvuloplasty catheter with a debris basket according to the present invention.

FIG. 4 illustrates another preferred embodiment of the present invention, in which an aortic valvuloplasty catheter 100 in accordance with the present invention includes a microporous filter basket 143. The aortic valvuloplasty catheter 100 is configured and operated in an almost identical manner as described previously. However, a microporous filter basket 143 is included proximal to the aortic sinus balloon 102 to catch any debris resulting from the valvuloplasty procedure and thereby prevent embolic complications in the patient. For example, aortic root or valve leaflet debris or thrombus may dislodge with the inflation of aortic sinus balloon 102. If these deposits or thrombus are not captured, e.g. by the microporous filter basket 143, such particles can travel to the brain, as well as other organs systems, causing stroke or other ischemic injury.

The microporous filter basket 143 is made up of multiple basket arms 142 which are pre-set in an expanded, open position. The proximal ends of the basket arms 142 are fixed to an anchor point on the enhanced aortic valvuloplasty catheter 100, while the distal ends of the basket arms 142 are self deployed against the ascending aorta 128. A microporous filter 141 is secured to the basket arms 142, creating an enclosed basket shape.

In operation, the microporous filter basket 143 remains packed within the sheath 124 while in a pre-deployed state. During this time, the basket arms 142 are pressed against the catheter body 106, while the microporous filter 141 is packed between the catheter body 106 and the sheath 124. When a user has positioned the aortic valvuloplasty catheter 100 at a desired location and wishes to deploy the microporous filter basket 143, the sheath 124 is retracted in a proximal direction, exposing the microporous filter basket 143 and allowing the pre-set basket arms 142 to expand and engage the aortic wall 128. Thus, if debris breaks loose during the valvuloplasty procedure, the filter basket 143 prevents this debris from traveling downstream into the vascular system. When the user removes the aortic valvuloplasty catheter 100, the sheath 124 is moved in a distal direction toward the filter basket 143 or the catheter 100 is retracted into the sheath 124, causing the filter basket 143 to compress in diameter and slide within the sheath 124.

The material constituting the filter basket may be comprised of the nanoskin material as disclosed in co-pending application Ser. No. 10/314,086, filed Dec. 6, 2002, entitled Covering And Method Using Electrospinning Of Very Small Fibers, the contents of which are incorporated by reference.

Single Balloon Valvuloplasty Catheter

Referring now to FIGS. 5A-5B, a single balloon valvuloplasty catheter 200 is illustrated, having a single catheter balloon 202 instead of two distinct balloons as in previously described embodiments.

Generally speaking, the single balloon valvuloplasty catheter 200 is configured with a similar structure to previously described embodiments. The single balloon valvuloplasty catheter 200 has a multi-lumen catheter body 204 with radiopaque markers 203 located at reference points on the distal portion of catheter body 204. A guidewire is positioned through a lumen within the catheter body 204 and extends out the distal end of the catheter body 204, which terminates in a pigtail shape 206. The catheter body 204 has a media port 201, positioned in the mid section of the catheter balloon 202, so as to allow communication with the media lumen in the catheter body 204.

The catheter balloon 202 preferably allows for progressive inflation, so that the distal anchoring section 202b of the catheter balloon 202 inflates before the proximal aortic portion 202a. This progressive inflation may be accomplished with catheter balloon sections having differing compliancy. For example, the distal anchoring portion 202b may have a relatively high compliance (e.g. about 2-4 ATM), while the proximal aortic portion 202a may have a relatively low compliance (e.g. about 4-8 ATM). Thus, as inflation media enters the catheter balloon 202, the more compliant section (i.e. the distal anchoring portion 202b) expands first. When the more compliant section fully expands, the pressure within the catheter balloon begins to increase further, allowing the less compliant section to begin expanding (i.e. the proximal aortic portion 202a). The balloon diameter of the proximal portion of the LVOT segment 202b, adjacent to the valve annulus 125, is restricted from growing substantially beyond the diameter of the annulus 125 by strategically positioning circumferential fiber reinforcement. In this manner, a user can precisely control the expansion sequence and maximal achieved diameter for each of the catheter balloon sections 202a, 202b.

When expanded, the proximal catheter balloon section 202a substantially conforms to the rounded contour of the aortic sinus root 123. By conforming closely to the aortic sinus root 123, the proximal catheter balloon section 202a may open the leaflets 126 by hyperextending them open as broadly as possible, reducing the possibility of tearing the valve annulus 125.

The compliance of each of the catheter balloon sections 202a, 202b can be obtained by utilizing fabric reinforcements at areas requiring additional strength. Preferably, fiber based membranes, as previously described in this application and in pending application Ser. No. 09/974,220 entitled Material Usable for Medical Balloons and Catheters (incorporated by reference), can be used to control the varying compliancy of the catheter balloon 202.

For example, referring to FIGS. 5D-5F, the balloon 202 in one embodiment may be designed such that the LVOT segment 202b of the balloon 202 is not fiber-reinforced and thus displays compliant characteristics as pressure is introduced into the balloon 202 while the proximal aortic portion 202a is fiber-reinforced (e.g., with yarns) and thus displays non-compliant characteristics. More specifically, in this one embodiment, the LVOT segment 202b is unreinforced and expands compliantly during an introduction of pressure P1 while the proximal aortic portion 202a includes a yarn reinforced sleeve configuration that forecloses expansion of the proximal aortic portion 202a until pressure within the balloon 202 reaches a predetermined pressure P2. Moreover, the fibers are configured so as to mechanically limit the enlargement of the proximal aortic portion to a predetermined size and shape, namely a size shape that conforms the proximal aortic portion 202a to the aortic root sinuses. Hence, in operation, when pressure P1 is introduced into the balloon 202, the LVOT segment 202b expands into the LVOT in a compliant manner and thus anchors the catheter in the LVOT. Then, when pressure P2 is reached, the proximal aortic segment 202a expands in a manner to perform the valvuloplasty, the yarn of the sleeve mechanically limiting the expansion (and thereby protecting the valve) to a predetermined shape and size.

In this regard, a taper zone 602 is designed into the balloon 200 configuration discussed above between the proximal aortic portion 202a and the LVOT segment 202b. This taper zone 602 has a narrower diameter than each of its adjacent sections and controls the medial "hip" shape of the balloon that is used to seat the balloon within the annulus of the valve and prevent excessive loads from being exerted by the balloon on the annulus during inflation.

Further in this regard, the fiber reinforcement in this embodiment could include polymeric yarns that are either fully oriented or partially oriented. Fully oriented yarns have characteristics that provide a high pressure mechanical "stop" and thus are particularly suited to creating balloon shape. Partially oriented yarns (POY) are slightly more compliant in the initial expansion stages and thus introduce a slight "stretch" characteristic into the expansion of the proximal aortic portion 202a. However, as the POY fibers become drawn, they become stronger. Therefore, the POY fibers can be configured on the proximal aortic portion 202a such that the POY fibers reach this "stronger" state at the same time the proximal aortic portion 202a reaches its desired size and shape and thereby mechanically limit further expansion of the proximal aortic portion 202a.

In the embodiment using the fully oriented yarns, it is preferable to use a knit structure since the knit structure could inherently introduce a degree of "stretchiness" into the sleeve that the fully oriented yarns may not otherwise provide. In the embodiment using the POY fibers, it is preferable to use a braid or weave of about 100-200 denier polyester yarns at 20-5-picks per inch for the braid embodiment and 40-6-picks per inch for the weave embodiment.

Figure 5I:
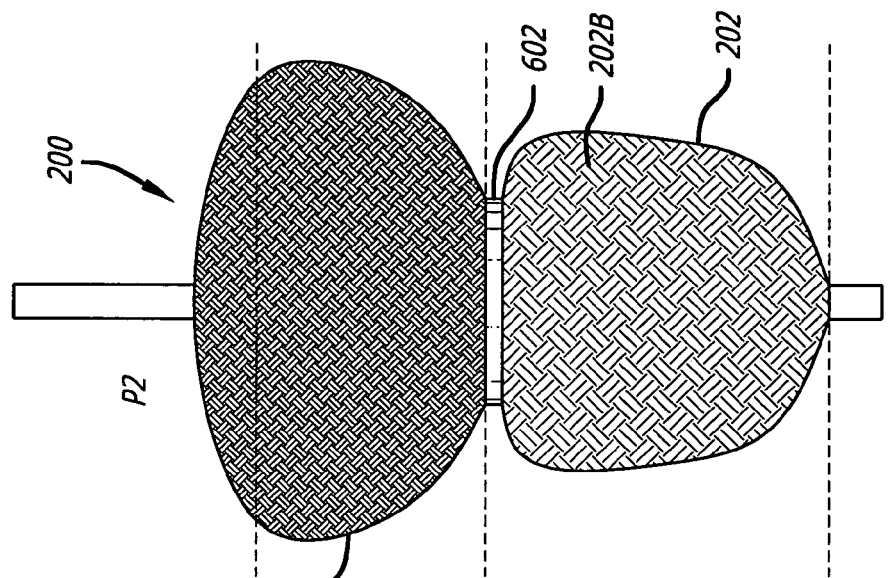
Figure 5H:
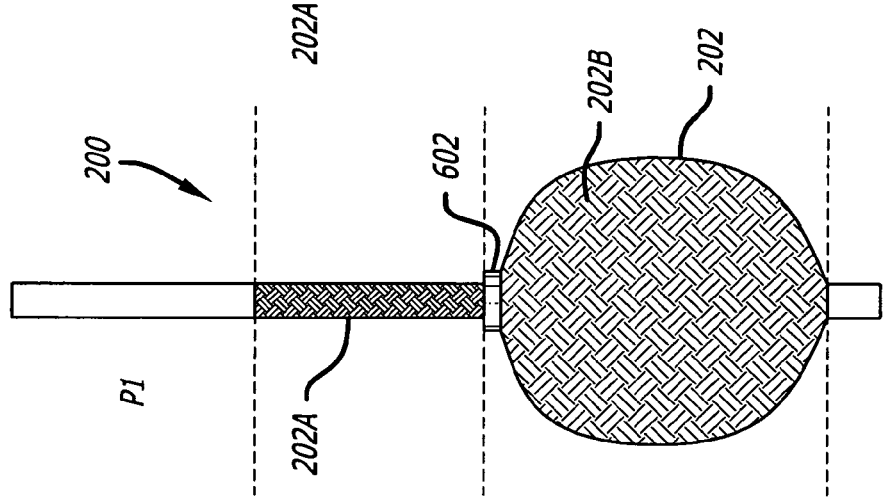
Figure 5G:
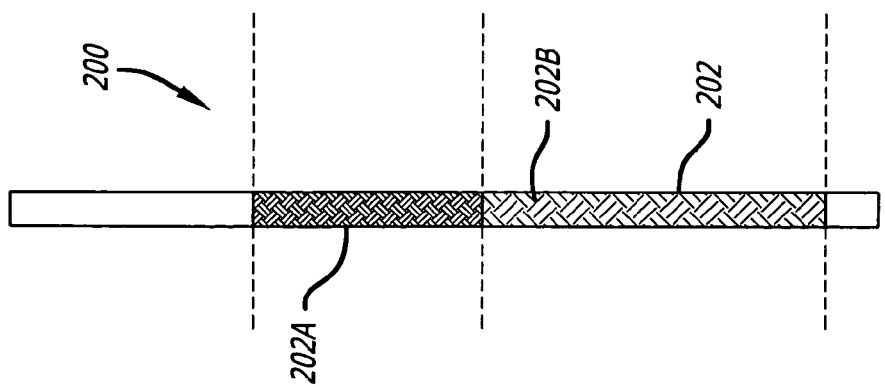

Referring to FIGS. 5G-5I, in a second embodiment, the LVOT segment 202b of the balloon 202 is fiber-reinforced such that it is either non-compliant or only partially compliant while the proximal aortic portion 202a is fiber-reinforced such that it exhibits compliant characteristics but only after a threshold pressure is reached. For example, the LVOT segment 202b may be comprised of a non-compliant or partially compliant PET or nylon plastic material while the proximal aortic portion 202a may be comprised of elastic filaments (e.g., spandex) that are compliant only after a threshold pressure. As a result, when pressure P1 is introduced into the balloon 202, the LVOT segment will resist expansion or only slightly expand until a pressure P1 is achieved, at which point the LVOT segment 202 will expand to a shape constrained by its PET or nylon plastic construction and which conforms to the LVOT. Then, when pressure increases to P2, the LVOT segment 202b will remain in its expanded state while proximal aortic portion 202a begins to expand in a compliant way as governed by the compliant properties of the elastic filaments. In other words, the elastic filaments hold or restrain the expansion of the proximal aortic portion 202a until the LVOT segment 202b expands and P2 is reached. Then the elastic filaments become loaded and start to stretch and expand in a compliant manner thereafter.

The elastic filaments in this second embodiment also create a textured surface that facilitates stability of the balloon 200 during the valvuloplasty. Furthermore the elastic filaments greatly assist in compressing the proximal aortic portion 202a to its initial uninflated sized so as to also greatly assist removal of the catheter after the valvuloplasty is complete.

In this second embodiment, the elastic filaments could comprise a braid of about 200 denier polyurethane filaments. In this regard, a braided fabric of elastic filaments would facilitate a greater range of expansion capabilities for the proximal aortic portion 202a. On the other hand, a woven fabric of elastic filaments would facilitate a more stable length expansion of the proximal aortic portion 202a. Furthermore, it should be recognized that the arrangement and makeup of the elastic filaments used in the proximal aortic portion 202a, e.g., filament size, fabric density, yarn tension, can be used to control the overall size and shape and inflation progression of the LVOT section 202b as well as the P2 activation pressure.

Figure 5L:
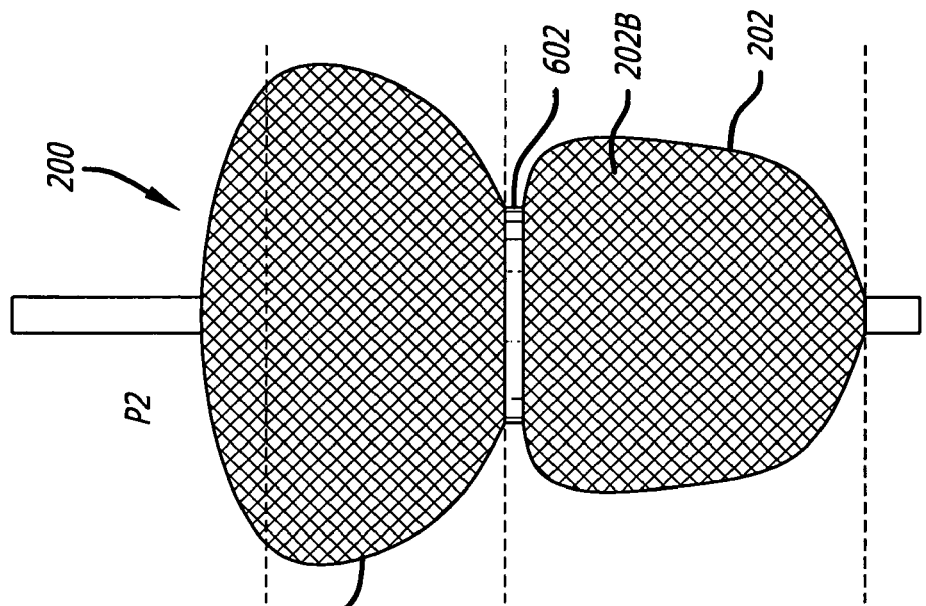
Figure 5K:
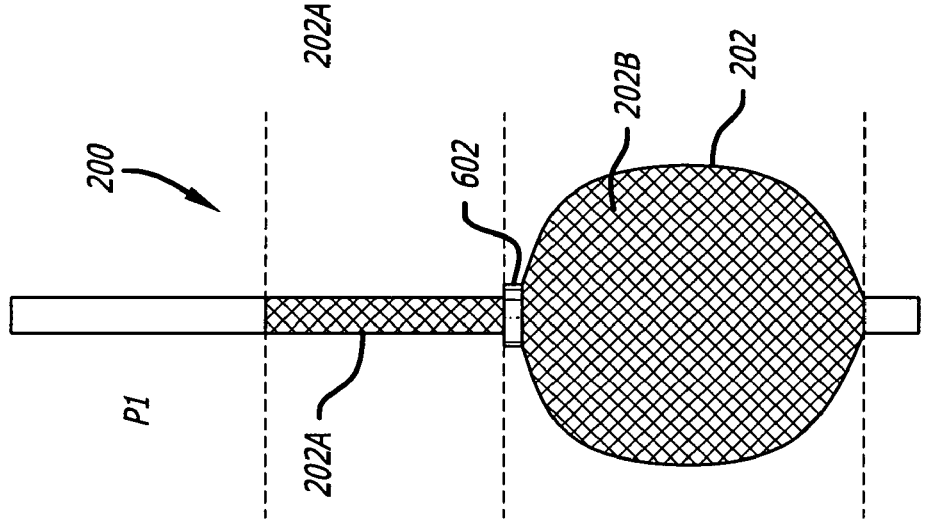
Figure 5J:
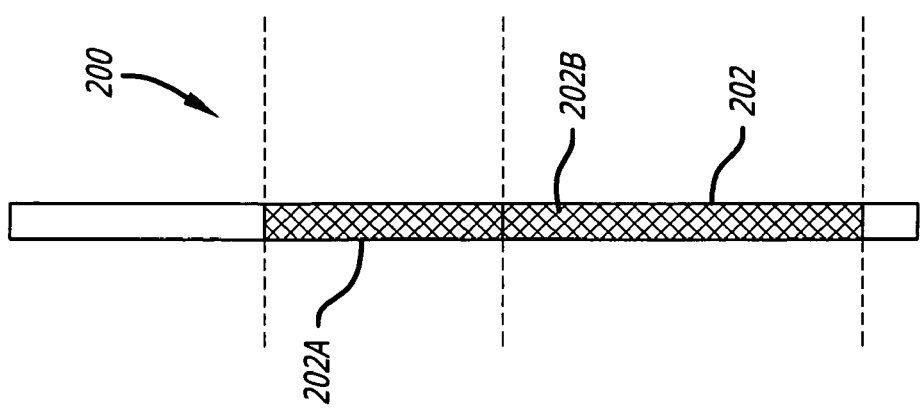

Referring to FIGS. 5J-5L, in a third embodiment, the balloon 200 may be a composite of a balloon membrane and a fabric with the fabric covering essentially the entire balloon membrane. The makeup of the fabric would control and govern the shape ultimately achieved by the balloon membrane and the makeup of the balloon membrane would control and govern the expansion system of the fabric. More specifically, the fabric would include fibers that limit the expansion of the balloon to certain predetermined shapes and sizes and the balloon membrane would include either different thicknesses or different material elasticity along its length so that the LVOT portion 202a expands prior to expansion of the proximal aortic properties 202b.

In this regard, in a preferred embodiment the fabric could be comprised of a 200-300 denier PET yarn that could be woven, knitted or braided and wherein the fibers are configured to control the expansion shape of the fabric. In a weave embodiment, the fabric is woven to match the expanded shapes as depicted in the Figures. In a braid embodiment, the fabric would be made by changing the braid angles over a shaped mandrel.

Also in this embodiment, the balloon membrane could be comprised of one material (e.g., silicone, polyurethane or some other highly elastic polymer) wherein the wall thickness at its LVOT portion is around 0.015 to 0.02 inches and the wall thickness in the proximal aortic portion is about 0.025 to 0.03 inches. Or in the alternative, the balloon membrane could be comprised of one material such as silicone but configure the silicone such that it has a durometer of around 10-15 A at the LVOT portion and a durometer of around 15-25 A at the proximal aortic portion. In some applications, it is conceivable that a durometer as high as 60 A could be used. Although a material with a durometer of this magnitude may be thick, it is conceivable that it could be used in a very thin cross section. In any event, a balloon membrane configured using this concept can control the preferential expansion of the LVOT section before the proximal aortic portion. In one embodiment, there may be no fabric at all and the expansion and shape characteristics of the balloon 200 are controlled by using different balloon materials, different balloon material hardnesses, and/or wall thicknesses to govern the expansion of the balloon.

With regard to the third embodiment of this section, a dual yarn system fabric could be used to create a compliant balloon system. "Wrapped" yarns typically comprise a polyurethane filament, such as spandex, with a high wrap per inch of polyester wrapped around it. As the polyurethane filament is stretched, the polyester yarns begin to unwraps or untwists from around the polyurethane until the polyester yarn is in tension. When this happens, the polyester yarn becomes a limitation on further stretching of the polyurethane. A woven, braided, or knitted wrapped yarn system using this approach would create a highly stretchy fabric with stretch limiting elements, namely, the polyester yarns. Changing the yarn density, or size of the yarns in the fabric will govern the activation pressures P1 and P2. Higher density fabric would require a higher activation pressure.

With regard to the fiber reinforcement constructions discussed above and elsewhere in the specification, it is likely that braids and weaves would be used although knits are possible as well. Braids and waves typically lead to more stable fabrics than knits an thus are better able to resist tension until a target pressure, e.g., P2, is reached, after which they will stretch and allow expansion.

With further regard to the fiber reinforcement constructions discussed above (and with regard to other embodiments of the present invention discussed elsewhere), it is noted that the fiber reinforcement approach allows the sealed portion of the device (the part that receives and contains the pressure for the purpose of expansion) can be very thin walled compared to prior art balloons and still tolerate high pressures. With the above described embodiments (and others not specifically identified), the wall of the sealed chamber can be as thin as 0.002 inches thick and can work in a pressure range of 2-20 atm.

It is also noted that the above embodiments (as well as other embodiments discussed in this application) could be configured such that the balloon 200 is actually comprised of two separate balloons instead of one balloon with two sections. In a two balloon embodiment, the same fiber reinforcement aspects discussed above could be used to achieve the expansion, shape and size characteristics that optimize the valvuloplasty being performed.

The distal anchoring section 202b of catheter balloon 202 is shaped similarly to the distal anchoring balloon 104 in FIG. 1. In this respect, the distal anchoring section 202b is located near the distal end of catheter body 204 and has a taper that increases in the axial, distal direction to closely conform to the LVOT 130. Note also that modification for the LVOT balloon 104 can be used for this distal LVOT segment 202b. The proximal aortic section 202a is also shaped similarly to the aortic sinus balloon 102 in FIG. 1, preferably conforming to the shape of the rounded aortic sinuses 123 when in an inflated state.

A long sheath 124 may be utilized for longitudinal stabilization of the catheter balloon 202 during inflation by abutting and pressing against the catheter balloon 202 in a distal direction. Since the inflated catheter balloon 202 tends to act as a sail, catching the antegrade flow of pulsatile blood flow from the heart, the sheath 124 can provide additional axial stability, reducing the tendency of the catheter balloon 202 to migrate.

In operation the single balloon catheter 200 is introduced through the femoral or brachial artery using a Seldinger technique with a vascular sheath introducer and a guidewire. After placement of the guidewire across the aortic valve, the single balloon catheter 200 is advanced retrograde over the guidewire such that the pigtail 206 is positioned in the left ventricle. Next, the distal anchoring section 202b is positioned, using fluoroscopy in combination with radiopaque markers 203, within the LVOT 130, just underneath the valve annulus 125. The distal anchoring section 202b is inflated with liquid contrast media which is communicated through an inflation port within the catheter balloon 202, best seen in FIG. 5A. The distal anchoring section 202b expands in diameter as inflation media is added, allowing it to press against the walls of the LVOT 130, thus longitudinally securing the position of the single balloon catheter 200. Once the distal anchoring balloon 202b is anchored securely within the LVOT 130, the proximal aortic section 202a is inflated by further increasing pressure within balloon 202, as seen in FIGS. 5B and 5C. It may be necessary to inflate the proximal aortic section 202a several times and at several graded diameters to achieve improved valve leaflet 126 flexibility and the desired pressure gradient reduction.

Alternatively, the single balloon catheter 200 may use a rapid exchange structure (not shown) having a guide wire which is generally located outside the catheter body 204. A portion of the guide wire passes through a short distal lumen (e.g. about 40 to 50 mm in length) located within the catheter body 204, distal to the catheter balloon 202. Thus, during a valvuloplasty procedure, the guide wire lies predominantly along side the catheter balloon 202 and catheter body 204 within the vessel except at the distal end of the single balloon catheter. This rapid exchange wire compressed between the balloon and vascular structures provides additional traction and stability to the catheter balloon 202 during expansion. Additionally, the catheter body 204 may have a lower profile since a guide wire lumen throughout the catheter body 204 is not needed.

FIGS. 11A and 11B illustrate yet another variation on the above described preferred embodiments, having two longitudinal and parallel catheter balloons 332 and 339. The overall inflated shape of the dual longitudinal balloon catheter 330 is similar to previously described embodiments, having a distal anchoring portion with an increasing taper in the distal direction for LVOT fixation and a rounded proximal portion for aortic valve dilation. Media ports 336 and 338 supply the inflation media to each catheter balloon 332, 339, while radiopaque markers 334 are used as references when positioning the dual balloon catheter 330. The dual catheter balloons 332, 339 may be inflated in a sequential manner. Sequential balloon inflation allows some antegrade blood flow with inflation of catheter balloon 332 and therefore less distal migration during the initial phase of inflation. Also, the inflated bi-lobed configuration can achieve more radial stretching of the leaflets in its greatest diameter. Also blood flow would be permitted in the recesses of both lobes of catheter balloons 332, 339 when inflated. Multiple sequential inflations can be carried out using radiopaque markers 334 to achieve different radial orientations to further improve valve leaflet flexibility and pressure gradient reduction.

As with the previous embodiment, the dual catheter balloons 332, 339 have differing compliance along their length, creating the overall inflated shape seen in FIG. 11A. As described above, the differing compliance is preferably achieved with fiber based membranes.

Referring now to FIGS. 12A-12C, a single umbrella balloon catheter 340 is shown, having a modified catheter balloon 342 shape. Single umbrella balloon catheter 340 is similar to the above described single balloon catheter 200 embodiment, except for the overall shape of catheter balloon 342.

As with the previously described embodiment, the differing shape of catheter balloon 342 is preferably controlled with fiber based membranes which allow for varying compliance of different portions of the catheter balloon. In the present preferred embodiment, the distal anchoring section 342b utilizes the fiber based membranes to create a curved "upside-down umbrella" shape, preferably about 6 mm in length with a distal to proximal taper ranging between about 14 mm to about 22-24 mm in diameter. The proximal aortic section 342a of balloon 342 is responsible for valve dilation and has an increasing taper in the distal direction of the catheter 340. The maximum inflated diameter is preferably about 24 mm to 30 mm toward the midsection. The LVOT section requires less media to fill, thus it will fill faster, allowing the arms of the distal anchoring section 342b to lock underneath the annulus 125 in the recess between the annulus 125 and the boundary of the adjacent LVOT.

Figure 13A:
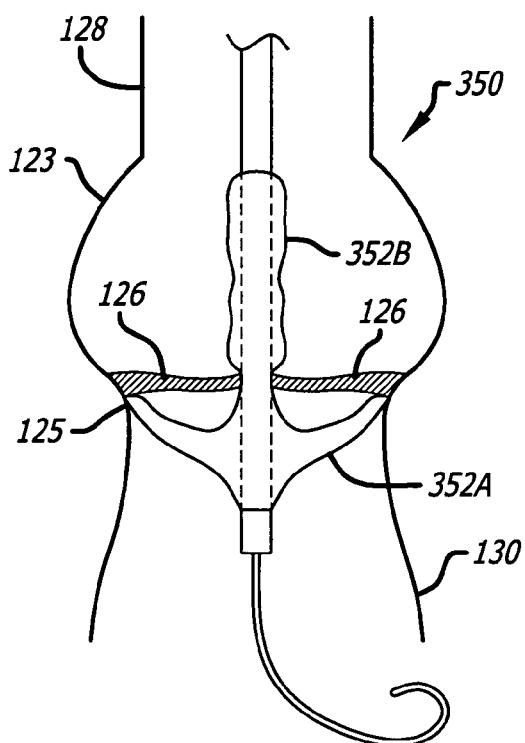
FIGS. 13A-13B illustrate side views of an valvuloplasty catheter according to the present invention.
Figure 13B:
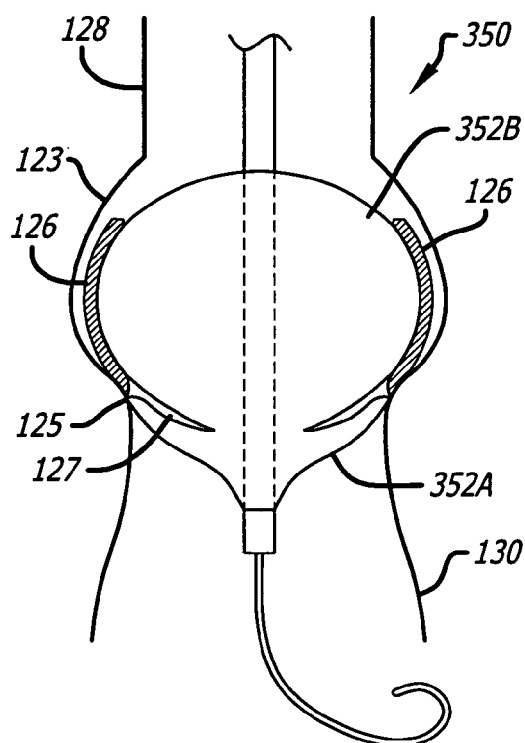

FIGS. 13A and 13B illustrate broad wing catheter 350, similar to the previous embodiment except for a broader, wing-shape of the distal anchoring section 352a. This broader wing shape of the distal anchoring section 352a reduces the likely hood of migration in the antegrade direction while the proximal aortic section 352b is being inflated. In addition, there remains a potential space 127 between the distal anchoring section 352a and the inflated proximal aortic section 352b which further reduces antegrade migration when segment 352b is inflated.

Balloon Catheter with Perfusion Channel

Turning to FIG. 8, yet another preferred balloon catheter 300 embodiment is shown, having a center perfusion channel 302a and possibly a one-way perfusion valve 304 at the proximal end of the center perfusion channel.

As with previously described embodiments, the catheter balloon 302 has a single chamber (or alternatively may have multiple balloon chambers), with a tapered distal region for engaging the LVOT and a rounded proximal region for expanding against valve leaflets 126 (not shown in FIG. 8). The catheter balloon 302 has varying compliance, as described with previous embodiments, to allow the distal region to expand first against the walls of the LVOT, locking the balloon catheter 300 in place. This is followed by expansion of the less compliant proximal region which conforms to the aortic sinuses 125 (not shown in FIG. 8), pressing against the valve leaflets 126.

The catheter balloon 302 is fixed to a multi-lumen catheter body in an off-center manner, as seen best in FIG. 8. With inflation of the catheter balloon 302 and expansion within the aortic root and LVOT, longitudinal movement is reduced by allowing perfusion through the central channel 302a.

The center channel 302a of catheter balloon 302 allows blood to perfuse distally through the catheter 300, thus increasing the amount of time the catheter balloon can be inflated without causing significant blood flow compromise. In addition, the central perfusion lumen improves longitudinal stability of the catheter balloon 302 position by allowing for a low resistance pathway for antegrade blood flow. To prevent back-flow of blood, a one-way valve 304 may be located at the proximal end of the perfusion channel 302a.

Alternatively, the one-way valve 304 can be located within the center of perfusion channel 302a, the distal end, or anywhere in between. Further, a one-way valve 304 may not be used in such an embodiment, as seen in the perfusion catheter 310 of FIG. 9. This perfusion catheter 310 similarly has a single channel 312a within the catheter balloon 312.

In yet a further alternative, the catheter balloon perfusion catheter 310 of FIG. 9 could be modified such that the catheter balloon 312 no longer has a LVOT distal portion or it has a truncated LVOT distal portion as shown in FIGS. 9A and 9B. In this embodiment, the balloon of the perfusion catheter 310 takes on more of a "donut" appearance.

Figure 22:
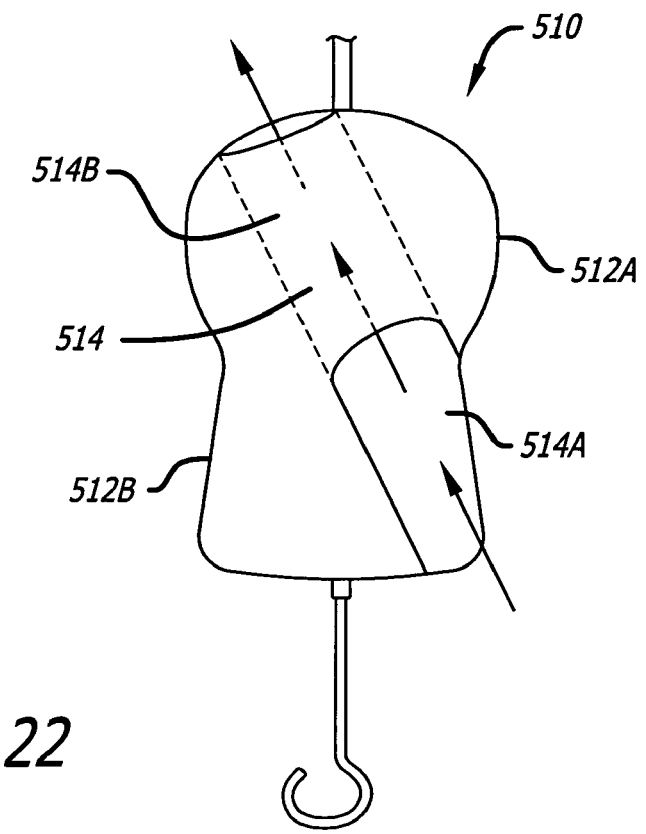
FIG. 22 illustrates a side view of an off center valvuloplasty catheter according to the present invention.

As seen in FIG. 22, a balloon perfusion catheter 510 may include an off axis perfusion channel 514, having an opened side 514a extending along the periphery of the anchoring section 512b and another opening at the proximal aortic section 512a. The perfusion channel 514 is positioned peripherally at the distal end of catheter balloon 510b, but is located centrally in the proximal aortic section 512b. Such an off axis perfusion channel 514 readily allows antegrade blood flow during both phases of balloon inflation, as indicated by the arrows seen in FIG. 22.

Referring now to FIGS. 10A and 10B, a similar single balloon catheter 320 is illustrated, having two or more side perfusion channels 322a along the periphery of the catheter balloon 322, instead of a single center channel. As with the previously described single chamber balloon catheters, this balloon catheter 320 is variably compliant to allow for initial expansion of the distal portion of balloon 322 to anchor within the LVOT. Further, the variable compliance assists in the creation of the perfusion channels 322a when the catheter balloon 302 is inflated. The perfusion channels 322a are less compliant than the other regions of the catheter balloon 322, which prevents the perfusion channels 322a from expanding outward in the same manner as the other regions of catheter balloon 322.

Additionally, the catheter balloon 322 may include internal supports (not shown) that maintain the inwardly angled shape of the perfusion channels 322a. For example, additional material within the catheter balloon 322 may secure portions of the perfusion channels 322a to the catheter body, preventing the perfusion channels 322a from expanding outward. Radiopaque markers 324 may be positioned on the outer radius of the catheter balloon 322 for reference markers, assisting a user with catheter positioning during a procedure, permitting, for example, multiple balloon inflations through a series of about 45 to 90 degree rotations. This would reduce the likelihood of creating gaps where portions of valve leaflets could migrate and therefore not be rendered more flexible.

As seen in FIG. 10b, the perfusion channels may include a membrane 321, covering the length of the perfusion channels 322a, yet leaving both distal and proximal perfusion channel 322a ends open. Thus, the perfusion channels 322a and membranes 321 form tube-like structures, providing greater structural support to the perfusion channels 322a yet still allowing perfusion. Membrane 321 additionally prevents gaps where the inflated balloon would otherwise not come in contact with the valve leaflets 126. Note the rounded and non-eccentric configuration of the catheter tip 323 which can be placed on balloon valvuloplasty catheters that need to be rotated through out a 360 degree arc during multiple inflation. This decreases the likelihood of resistance to rotation created by the previously noted pigtail configurations.

Figures 21A, 21B:
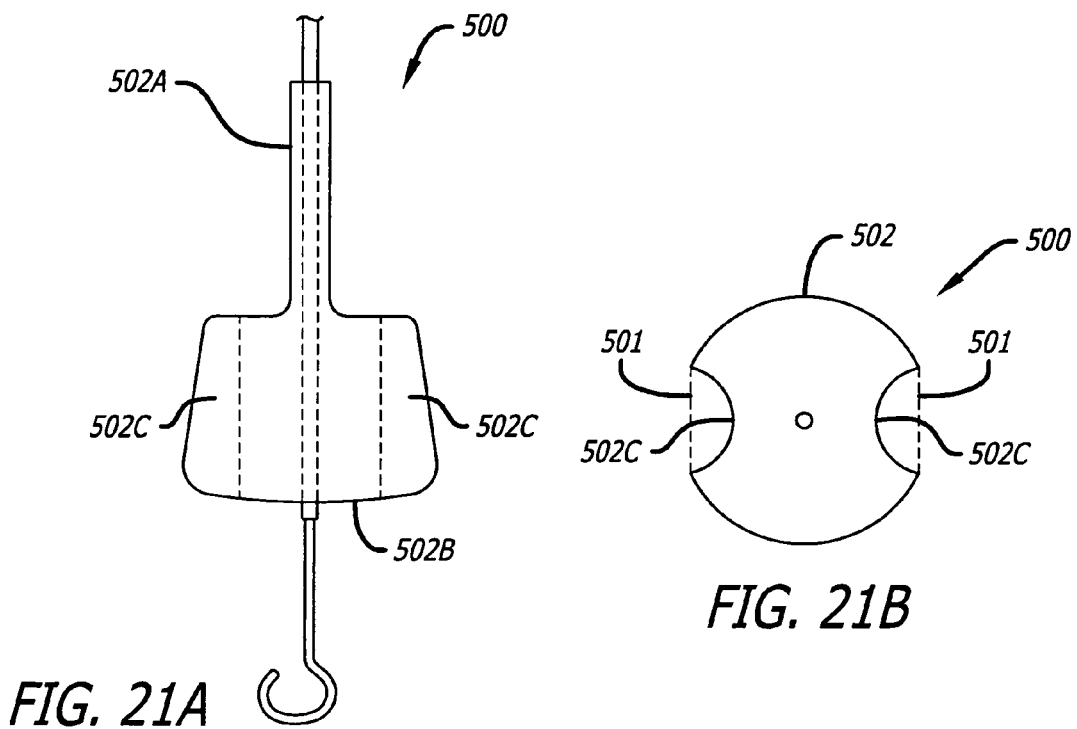
FIG. 21A illustrates a side view of an valvuloplasty catheter according to the present invention.
FIG. 21B illustrates a bottom view of the valvuloplasty catheter of FIG. 21A.
Figures 21C, 21D:
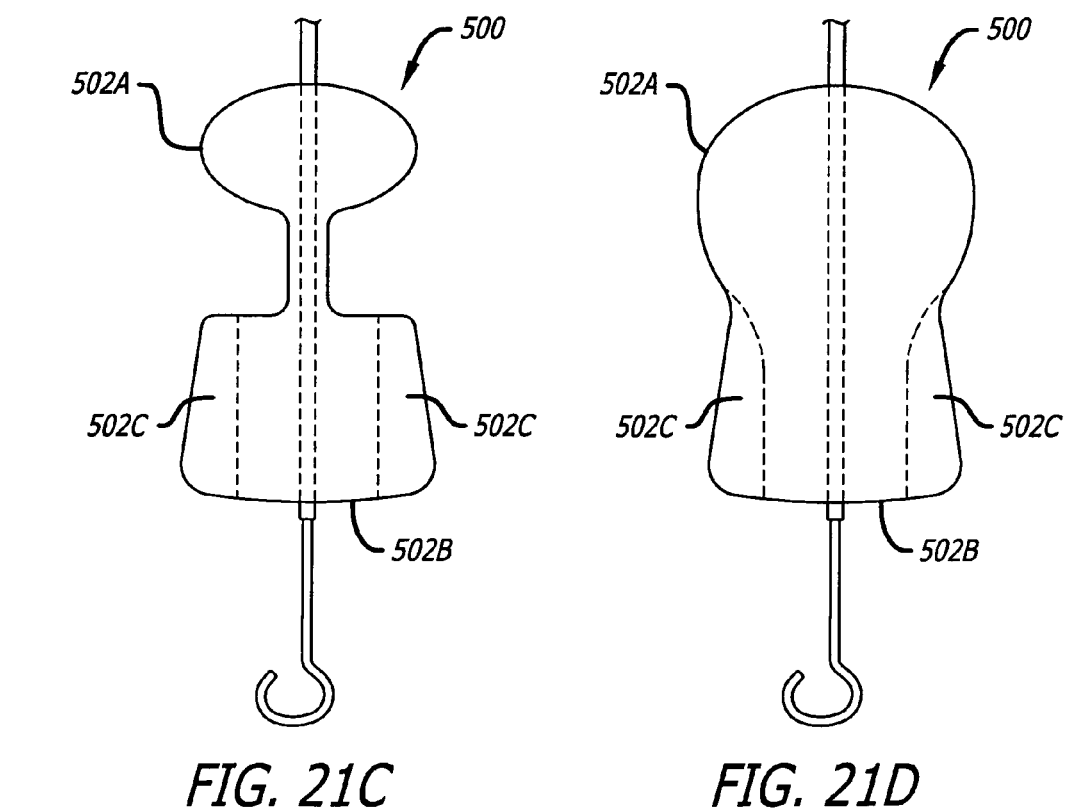
FIG. 21C illustrates a side view of the valvuloplasty catheter of FIG. 21A.
FIG. 21D illustrates a side view of the valvuloplasty catheter of FIG. 21A.

FIGS. 21A-21D illustrate an enhanced catheter 500 design similar to that shown in FIGS. 10A and 10B. However, the enhanced catheter 500 includes a single catheter balloon 502 having perfusion channels 502c along the margins of the distal anchoring section 502b only and specifically do not extend across the aortic segment 502a. As with previous embodiments, the distal anchoring section 502b inflates first, expanding against the LVOT. The perfusion channels 502c are inwardly curved longitudinal conduits which allow blood to flow around the anchoring section 502b during a procedure. The perfusion channels 502c may be enclosed by a membrane 501, as seen in FIG. 21B. The membrane 501 forms longitudinal tubes which can have a single channel or multiple channels, with an overall linear or spiral shape.

Figure 21E:
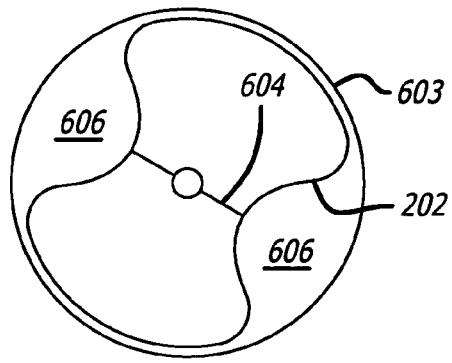
FIGS. 21E-21K illustrate various top and side views of a valvuloplasty catheter that has perfusion channels which are formed by fiber reinforced structures in accordance with the present invention.

With reference to FIGS. 21E-21K, yet further embodiments of a catheter design having perfusion channels is disclosed. In this regard, these embodiments are especially suited to the balloons using fiber reinforcement to control expansion and shape characteristics of the catheter (e.g., the embodiments of FIGS. 5A-5L). Referring to FIG. 21E, a balloon 202 may be configured to have a strap 604 that connects internally across opposing internal surfaces of the balloon 202. The strap 604 is in tension and thus constrains the opposing surfaces of the balloon from fully expanding. As a result, perfusion channels 606 are created by the balloon 202 within the body lumen 602 where the device is placed.

Figure 21F:
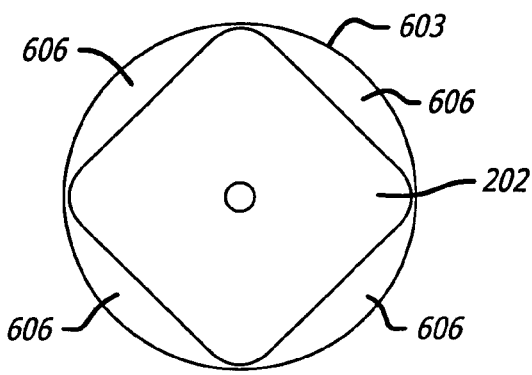

Referring to FIG. 21F, the balloon 202 could be fabricated such that fiber reinforcement of the balloon requires the balloon 202 to take on a non round shape (e.g., a star shape, a triangular shape or a square shape) when inflated. This too results in the formation of perfusion channels 606.

Figure 21G:
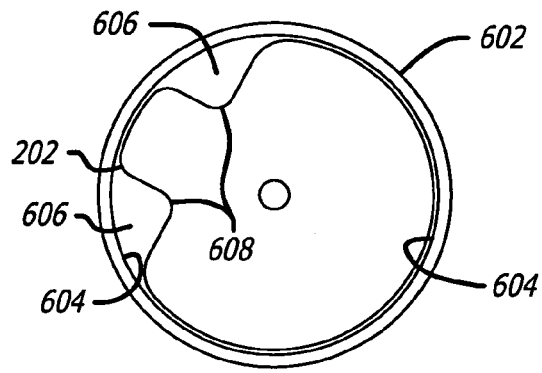
Figure 21H:
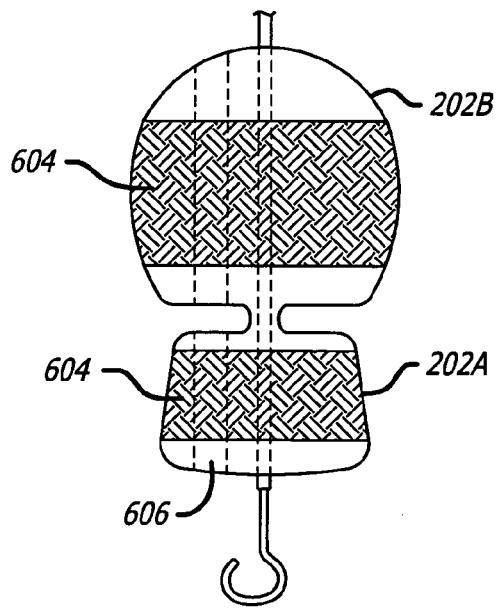

Referring to FIGS. 21G and 21H, the balloon 202 could be configured with a strap or straps 604 that are adhered to the external surface of the balloon 202. Furthermore the straps 604 would constrain the expansion of the balloon 202 such that the balloon "buckles" at certain locations at certain pressures. This "buckling" would lead to "buckle zones" 608 that also would serve to create perfusion channels 606. In this regard, FIG. 21H depicts a strap as it would surround the proximal section 202b and as a strap would surround the distal section 202a of the balloon 202 to create the aforesaid "buckle zones."

Figure 21I:
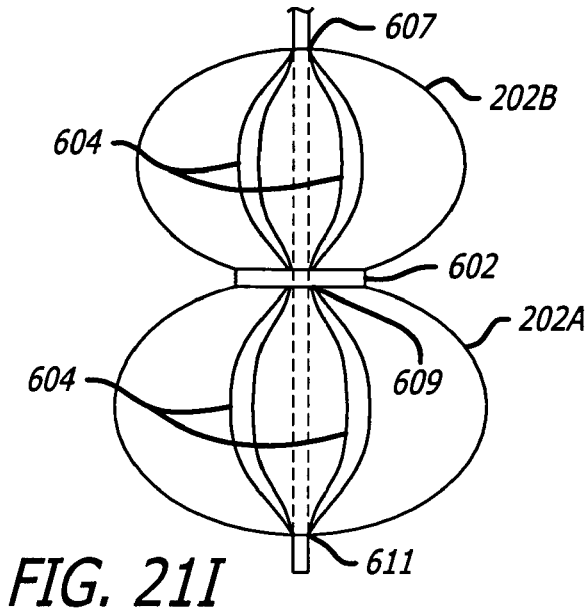
Figure 21J:
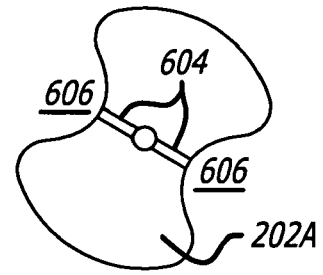
Figure 21K:
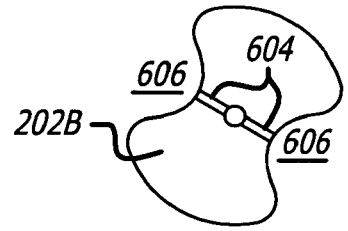

FIGS. 21I-21K depict an embodiment wherein the distal end 609 the proximal section 202b and the distal end 611 of the distal segment 202a of the balloon 202 are each movable relative to the proximal end 607 of the proximal section 202b and the proximal end 609 of the distal segment 202a, respectively. Alternatively, each section of the balloon could be a separate balloon wherein the distal end of each balloon is movable along the catheter shaft. Furthermore, a plurality of straps 604 extend from the proximal to distal end of each balloon segment and each end of each strap is connected to the catheter shaft.

Hence, when, for example, the distal segment 202a of the balloon 202 begins to expand, the distal end 611 of the distal segment 202a will begin to move toward the proximal end of the catheter. This will allow the distal segment 202a to begin to increase in diameter while becoming shorter in length. However, the presence of each strap 604 will constrain the increasing size of the distal segment 202a in a way as shown in FIG. 21J such that perfusion channels 606 are created. Similarly, as shown in FIG. 21K, as the proximal segment 202b inflates, it too will be constrained by the straps 604 so that the proximal segment 202 also is forced to create perfusion channels 606.

In a preferred embodiment, the straps discussed above would be made from a thin wall woven polyester fabric. It would be a band of around 60 Denier by around 2 mm.

Ring and Balloon Catheter

FIGS. 6A-6C illustrate yet another preferred embodiment of the present invention, this embodiment including a ring and balloon catheter system 250 for creating multiple flexible hinge points in the valve leaflets 126. The ring and balloon catheter 250 acts to "pinch" the valve leaflets 126 between an expandable ring 254 and a balloon 258.

The expandable ring 254 is self expanding, being controlled with ring arms 256 fixed to the circumference of the ring 254. The ring arms 256 are slidably positioned within a lumen of the catheter sheath 252 and extend out of the distal end of the sheath 252 through movement of the control lever (not shown), allowing a user to push the ring 254 away from the catheter body 252. In a retracted state, the ring arms 256 maintain the diameter of the ring 254 at a minimum size. When the ring arms 256 push the ring 254 in a distal direction, the diameter of the ring 254 expands.

A catheter balloon 258 is in communication with a media inflation lumen. The balloon catheter 258 operates independent of the sheath 252 and its advanceable ring 254. In other words, the ring 254 with its ring arms 256 can be advanced and retracted independently of advancement and retraction of the balloon catheter 250. The balloon is elongated in shape when inflated, expanding within, and pressing the valve leaflets against the inside of ring 254. Preferably, the catheter balloon 258 has an inflated diameter no greater than about 1-2 mm's larger than the ring to prevent avulsion of the leaflets 126.

In operation, the user positions the distal end of the catheter 250 within the aorta 128 just above the aortic valve leaflets 126. Next, the ring arms 256 are deployed outward in a distal direction from the catheter sheath 252, causing the ring 254 to expand. The user positions the expanded ring 254 on the aortic surface of the valve leaflets 126. Next, balloon catheter 250 is advanced and balloon 258 positioned within both leaflets 126 and ring 254. Media is then injected through a media lumen within the catheter body 250 to inflate catheter balloon 258. As the catheter balloon 258 expands, it presses against the ring 254 and leaflets 126, pinching and bending the leaflets 126 to create a hinge point 126a, as shown in FIG. 6C. The formation of these hinge points allows for more broad leaflet opening and thus better passage of blood through the valve. This procedure may be performed multiple times with different ring diameters to create multiple hinge points 126a on the valve leaflets 126. When finished, the user merely deflates the catheter balloon 258 and retracts balloon catheter 250 into the sheath 252. Ring arms 256 are then retracted within the delivery sheath 252, which is subsequently then removed from the patient.

In addition, the expandable ring 254 may be mounted with tiny apertures along its internal circumference which can be used to infuse locally delivered drugs, for example, antirestenotic drugs into the aortic surfaces of the valve leaflets 126 pinched between the ring 254 and inflated catheter balloon 258. The ring lumen may be connected to an infusion port at the proximal end of the sheath and may extend the length of the sheath within one or more of the ring arms 256.

Balloon Catheter with Wires

Referring now to FIGS. 7A and 7B, another preferred embodiment of the present invention is illustrated, having three longitudinal wires 272 (although they can occur in any number, including 2 or more than 3) which are expanded with balloon 274 inflation to anchor and prevent balloon slippage across the aortic valve. The tripod wire catheter 270 contains a catheter balloon 274 which expands underneath the longitudinal wires 272, pushing them outwards preferably, although not necessarily, into the commissures of the valve. The balloon 274 can be simply fusiform in shape or be configured with multiple segments as described for the embodiments previously discussed.

The three longitudinal wires 272 are fixed to two wire mounting rings 278, one or the other of which is secured to the catheter body 276, for example the proximal ring 278a. The nonfixed wire mounting ring 278b can slide along the catheter body 276, allowing the longitudinal wires 272, which are not along their length attached to the balloon surface, to bow outwards or lie flat against the catheter body 276. Positioned underneath the longitudinal wires 272 is a catheter balloon 274 which communicates with an inflation media lumen within the catheter body 276.

In operation, the tripod wire catheter 270 is positioned across the aortic valve leaflets 126. Next, the catheter balloon 274 is inflated, expanding against both the longitudinal wires 272 and the leaflets of the valves. As the catheter balloon 274 presses against the longitudinal wires 272, the wires 272 expand out with at least part of the balloon 274 conforming to the aortic sinuses and adjacent LVOT, creating points of increased friction between the balloon 274 and leaflets 126, that prevent slippage. Additionally, these longitudinal wires 272 concentrate lines of force to enhance fracturing of the calcified leaflets and possibly separate occasionally fused commissures.

Petal Anchoring Catheter

Figure 14A:
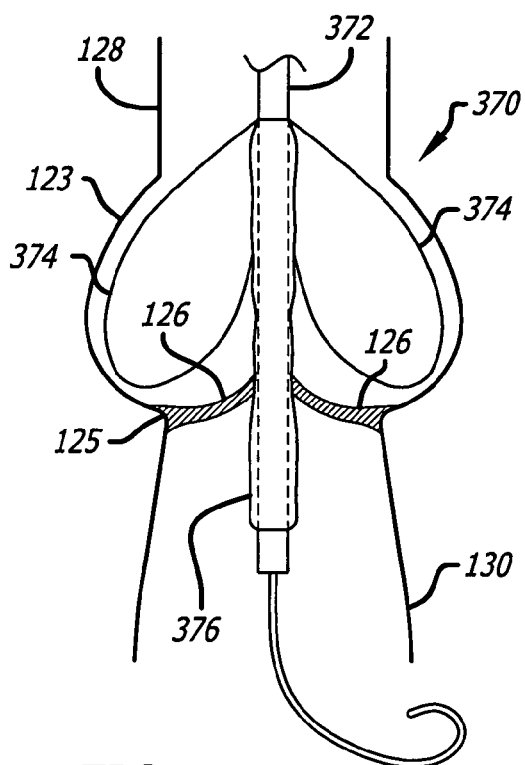
FIG. 14A illustrates a side view of a petal anchoring catheter according to the present invention.
Figure 14B:
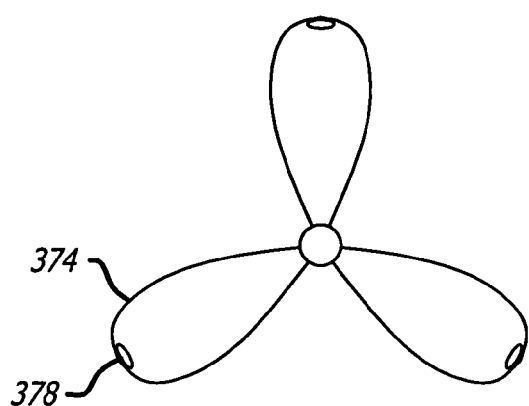
FIG. 14B illustrates a top view of petals of the petal anchoring catheter of FIG. 14A.

FIGS. 14A and 14B illustrate yet another preferred embodiment of the present invention, this embodiment including petal anchoring catheter 370, having expandable anchoring petals 374 which expand against the aortic root walls 128, laterally and inferiorly in the inferior recesses of the aortic valve sinuses. This will stabilize and prevent movement of the petal anchoring catheter 370 before and during balloon inflation. Once anchored, the catheter balloon 376 inflates to push the valve leaflets 126 against the anchoring petals 374 and adjacent the aortic root walls 123.

The expandable anchoring petals 374 are preferably composed of nitinol, pre-set to expand to an open position. Each anchoring petal 374 has a radiopaque marker 378 at its end for reference when positioning the petal anchoring catheter 370. The expandable anchoring petals 374 are packed within a sheath (not shown) while being advanced through a patient's vascular system.

Since the anchoring petals 374 have a basic wire-frame structure, they permit simultaneous catheter 372 fixation and perfusion while balloon 376 is uninflated. This allows the petal anchoring catheter 370 to be left in place for extended periods of time. Further, the catheter balloon 376 may have perfusion conduits previously described in this application to allow for additional perfusion during balloon inflation.

The anchoring petals 374 may be fixed at a specific length away from the catheter balloon 376 or may be decoupled to allow for additional adjustment during a valvuloplasty procedure. To reduce aortic root trauma, the anchoring petals 374 are preferably somewhat flexible, allowing for a "soft" engagement with the aortic root wall 123.

In operation, the petal anchoring catheter 370 is positioned so that the catheter balloon 376 passes through the aortic valve. Next, the anchoring petals 374 are deployed, engaging the aortic root wall 123 and the inferior recesses of the aortic sinuses near the annulus 125, preventing the petal anchoring catheter 370 from longitudinal movement. Finally, the catheter balloon 376 is inflated so as to push open the valve leaflets 126. The catheter balloon 376 is then deflated but may be reinflated multiple times to achieve a desired leaflet flexibility and pressure gradient reduction. When this has been achieved, the anchoring petals 374 are retracted and the petal anchoring catheter 370 is removed from the patient.

Figure 15A:
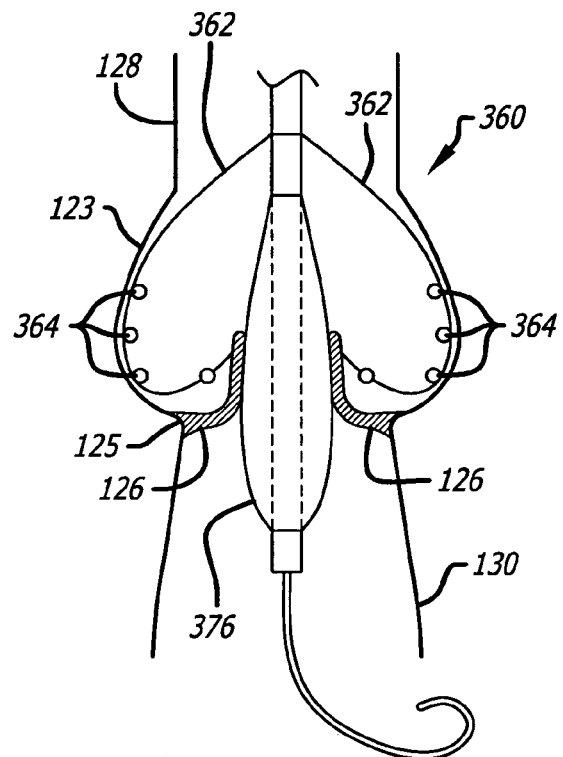
FIGS. 15A-15B illustrate a petal anchoring catheter according to the present invention.
Figure 15B:
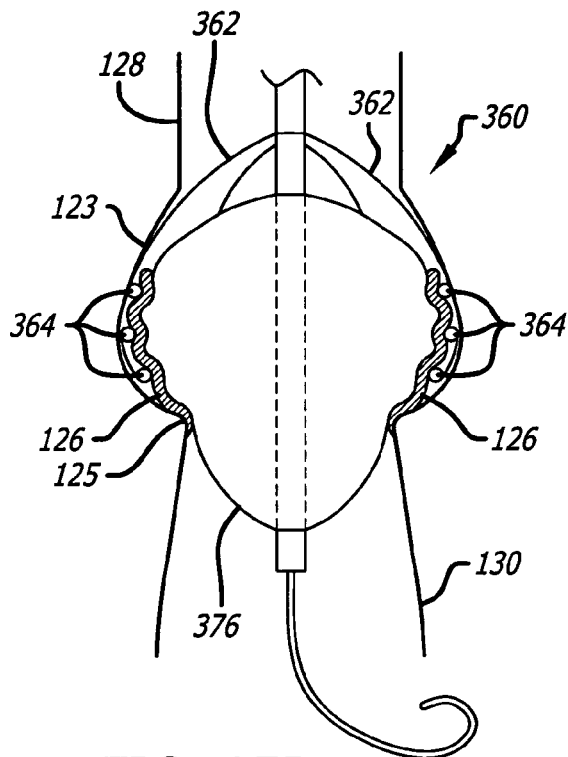
Figure 15C:
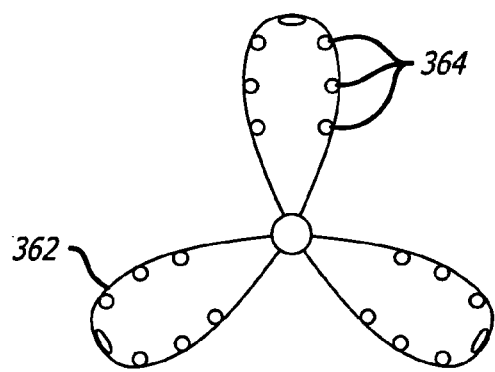
FIG. 15C illustrates a top view of petals of the petal anchoring catheter of FIG. 15A.

In an alternative preferred embodiment shown in FIGS. 15A-15C, a petal anchoring catheter 360 similar to the previously described embodiment is shown having stress risers 364 along the wires of anchoring petals 362. These stress risers 364 allow multiple hinge points to be created along the valve leaflet 126.

During a valvuloplasty procedure, the petal anchoring catheter 360 is positioned within an aortic root 123 and the anchoring petals 362 are deployed in the aortic root 123 immediately proximal to the valve leaflets 126. Next, the catheter balloon is inflated, expanding the valve leaflets 126 against the anchoring petals 362 and the stress risers 364, best seen in FIG. 15B. The stress risers 364 create points of stress concentration behind the leaflets 126, allowing for multiple hinges in the leaflets 126 to be more easily created to further enhanced leaflet flexibility.

It should be noted that the petal anchoring catheter 370 of FIGS. 14A and 14B may be additionally used to hold a valve open for other procedures or create points of friction between the balloon 376 and the leaflets 126 to prevent slippage. In this manner, the anchoring petals 374 are positioned along the ventricular surface of the valve leaflets 126 and expanded with balloon 276 inflation, pressing the leaflets 126 into the aortic root sinuses. Additionally, the petal anchoring catheter 360 and 370 may be used as a fixed platform on which prosthetic implants can be delivered to and deployed on the aortic valve.

Mesh Anchoring Ring

Turning now to FIGS. 23A-23C, a balloon catheter 550 is illustrated according to the present invention, having an expandable mesh anchoring disk 556. As with many of the previously described embodiments, the balloon catheter 550 anchors within the LVOT when the mesh anchoring disk 556 expands to press against the walls of the LVOT.

The mesh anchoring disk 556 is expandable and preferably made from a plurality of semi-rigid, elongated elements which form a mesh. The mesh anchoring disk 556 may be expanded by a trigger wire or cable (not shown) which moves either the distal or proximal end of the mesh anchoring disk 556 relative to the opposing end, thus expanding or contracting the shape. Since the mesh anchoring disk 556 is composed of a mesh-like material, blood is able to perfuse through.

In operation, catheter 550 is advance over a guide wire through a vascular introductory sheath. The user utilizes radiopaque markers 554 to position the balloon catheter 550 as previously described in this application. Once the mesh anchoring disk 556 is positioned at the LVOT, the user anchors the balloon catheter 550 by expanding, i.e. activating the mesh anchoring disk 556, engaging the wall of the LVOT. The catheter balloon 552 is then inflated a desired amount to open the valve leaflets 126. Next, the catheter balloon 552 is deflated and the mesh anchoring disk 556 is contracted, i.e. inactivated, allowing the balloon catheter 550 to be removed from the patient.

Alternately, the mesh anchoring disk 556 may be self expanding and may optionally have compliant apices to prevent injury to the aortic valve. The balloon catheter 550 may be further used as a fixed platform on which prosthetic implants can be delivered to and deployed on or adjacent to the aortic valve. These prosthetic implants may include prosthetic valves, drug eluting or similar devices. In addition, this fixed platform can be used to deliver and position high energy sources for debulking valve leaflets such as excimer lasers, high energy low frequency ultrasound and radio frequency.

Drug Delivery Devices

The valvuloplasty procedures described in this application generally involve the application of significant amounts of force on the aortic valve leaflets. It is well known in the art that such force and/or similar trauma can cause restenosis of the valve, leaving the valve leaflets again stiff and inflexible. In this manner, eventual loss of the improved valve opening occurs with return of the initial transvalvular pressure gradient.

To this end, it is desired to deliver drugs, temporarily position brachytherapy sources, or other locally delivered therapeutic substances to the aortic valve to prevent or moderate aortic valve restenosis or even progressive stenosis. One method of delivering such drugs is by way of a local drug eluting implant.

For example, a drug eluting implant may deliver paclitaxel or any other taxane/taxane derivate, rapamycine, or a rapamycin derivative, flurouracil, other pharmacological agents, anti-mitotics, anti-proliferatives, proteins, genes, gene therapy vectors, RNA/nucleotides or any other agent that prevents the valvular restenosis process. Further, such a device may elude decalcification agents as well as agents to limit or reverse collagen deposition and in this manner cause favorable remodeling of the valve leaflets and thereby reverse stenosis. Such devices may also eliminate thrombus/inflammation/calcification.

Turning to FIG. 16, a flexible finger implant 400 is shown having an anchoring ring 402 and a plurality of drug eluting fingers 404. The anchoring ring 402 seats within the LVOT adjacent to the valve annulus 125 with the drug eluting fingers 404 angled towards the valve leaflets 126. The drug eluting fingers 404 contact the valve leaflets 126, eluting a desired anti-restenosis drug or substances as listed above. The flexible finger implant 400 may be delivered by the valvuloplasty catheter embodiments described in this application, modified to include implant delivering mechanisms, or a separate implant delivery catheter may be used.

FIGS. 17A and 17B illustrate another embodiment of an implant 410 which includes an anchoring ring 411 and T-shaped drug eluting pods 412. The anchoring ring 411 engages the LVOT adjacent to the valve annulus 125 while the T-shaped drug eluting pods 412 are fixed to the anchoring ring 411 and pass proximally through the commissures of the valve, allowing the elongated horizontal portion of the T-shaped drug eluting pods 412 to contact the aortic side of each leaflet 126 base. By contacting the valve leaflets 126, the T-shaped drug eluting pods 412 are able to transfer in a time dependent manner, anti-restenosis drugs to the leaflets 126. The horizontal arms of the T shaped pods 412 pinch the valve leaflets between these extensions and the ring on the LVOT side, helping to preserve a stable position to prevent dislodgment. The T-shaped pod implant 410 may be delivered by the valvuloplasty catheter embodiments described in this application, modified to include implant delivering mechanisms, or a separate implant delivery catheter may be used.

Note that variations on the T-shaped pod implant 410 are possible, such as the L-shaped pod implant 414 seen in FIG. 18, having L-shaped drug eluting pods 416 which pass through the commissures of the valve to contact the leaflet 126 base. Further, finger extensions such as these seen on the device in FIG. 16, can extend from either the ring 411 or the T shaped pods 412, to increase the surface area from which additional drugs can be delivered.

In yet another preferred drug eluting embodiment, FIG. 19 illustrates drug eluting posts 420 having single or dual barbs. A puncture or multiple punctures are preferably created in each valve leaflet 126 by way of radio frequency, laser, high energy low frequency ultra sound, or other devices to allow the drug eluting post to be easily pushed into the valve leaflets 126. The barbs on one or both ends of the drug eluting posts 420 prevent the drug eluting posts 420 from sliding out of the apertures within the leaflets 126.

Optionally, the above described drug eluting devices may be composed of a bioabsorbable material which allows the device to be absorbed over time. Additionally, the drug eluting devices may be composed of a metal or polymer mesh which allows cells to infiltrate and colonize, allowing the mesh to become a "living structure".

Post Valvuloplasty Therapy

One of the limitations in valvuloplasty procedures, and particularly in aortic valvuloplasty procedures, is the high probability of restenosis, with restenosis being generally reported in the literature to range from 40% to 80% at six months. Although the mechanism of restenosis is not well defined, it may at least in part be related to a process of pathologic bone formation known as heterotopic ossification. It is also suspected that granulation tissue and scar formation (i.e., hypertrophic scar formation) likely contribute to restenosis.

In connection with restenosis after angioplasty in the coronary artery and/or peripheral artery, brachytherapy has been used in the past as a preventative therapy. However, restenosis in coronary or peripheral arteries is due primarily to neointimal formation, a response which is not believed to play a significant role in aortic valve restenosis.

On the other hand, it is known that external radiation therapy is routinely used in non-cardiovascular applications for treating heterotropic ossification and hypertrophic scar formation. And given the role that ossification and scar formation are suspected to play in aortic valve restenosis, the inventors conceived of utilizing such external radiation therapy on patients who have successfully completed aortic valvuloplasty. In this regard, the inventors have conducted a trial of this post valvuloplasty radiotherapy with successful midterm results.

Our trial evaluated the treatment of twenty patients who underwent external beam radiotherapy following balloon valvuloplasty. A 6 month followup of ten patients demonstrated a restenosis rate of about ten percent. This compares to a historical restenosis rate of 50-80%.

Although it is likely that several different external beam radiation therapy strategies may be applied, in one preferred embodiment, the therapy would include using an anterior/posterior and posterior/anterior window and applying a total dose of 12-18 Gy delivered in fractions over a 3-5 day period.

Finally, it is readily apparent that the external beam radiation therapy described herein can be utilized with essentially any of the valvuloplasty devices disclosed herein. As such, it is clear that the present invention extends not only to valvuloplasty per se, but also to the methods of ensuring the long term success of the valvulopasty.

Although the invention has been described in terms of particular embodiments and applications, one of ordinary skill in the art, in light of this teaching, can generate additional embodiments and modifications without departing from the spirit of or exceeding the scope of the claimed invention. For example, although the application emphasizes the invention as it may be utilized in performing aortic valvuloplasty, it should be understood that the invention as disclosed and contemplated by the inventors has far greater applicability and utility valvuloplasty alone. For example, the invention has applicability in various vascular applications and other restrictions in the vascular system (e.g., venous valves, other heart valves, urinary tract constrictions, coronary restrictions, etc.). Accordingly, it is to be understood that the drawings and descriptions herein are proffered by way of example to facilitate comprehension of the invention and should not be construed to limit the scope thereof.

What is claimed is:

1. A method of performing aortic valvuloplasty comprising:
   providing a catheter having a balloon;
   advancing said catheter towards an aortic valve;
   expanding a first region of said balloon to a first maximum inflated diameter so as to contact a patient's ventricular outflow tract to reduce downstream migration of said balloon;
   expanding a second region of said balloon to a second maximum inflated diameter so as to hyperextend a patient's valve leaflets against an aortic sinus; and,
   expanding a third region of said balloon to a third maximum inflated diameter that is smaller than said first and second maximum inflation diameter and substantially equal to a diameter of a patient's valve annulus so as to prevent dissection of said annulus;
   wherein said third region is located between said first region and said second region.

2. The method as set forth in claim 1, wherein said first region expands at a first media pressure and said second region expands at a second media pressure.

3. The method as set forth in claim 1, wherein said first region has a first compliancy, said second region has a second compliancy and said third region has a third compliancy.

4. The method as set forth in claim 3, wherein said first region expands prior to expansion by said second region.

5. The method as set forth in claim 1, further comprising, allowing perfusion of blood past said expandable member.

6. The method as set forth in claim 1, further comprising measuring a pressure proximal and distal to said aortic valve.

7. The method as set forth in claim 1, further comprising depositing an anti-restenosis agent in a region of said aortic valve.

8. The method according to claim 1, further comprising:
   providing a sheath movable over said catheter such that movement of said sheath controls exposure of said balloon; and,
   stabilizing said balloon with said sheath after expanding said balloon.

9. The method of claim 1, wherein said first and second media pressures are substantially equal.

10. A method of treating a heart valve comprising:
    identifying a target heart valve having diseased leaflets;
    delivering a balloon an at said diseased leaflets; and,
    expanding a first region of said balloon to a first maximum inflated diameter so as to engage a patient's ventricular outflow tract to reduce downstream migration of said balloon;
    expanding a second region of said balloon to a second maximum inflated diameter so as to hyperextend a patient's valve leaflets against an aortic sinus; and,
    expanding a third region of said balloon to a third maximum inflated diameter that is smaller than said first maximum inflated diameter and second maximum inflated diameter and not greater than a diameter of a patient's valve annulus so as to prevent distension of said annulus
    wherein said third region is located between said first region and said second region.

11. A method according to claim 10, wherein said first region expands at a first media pressure and said second region expands at a second media pressure.

12. A method according to claim 11, wherein said first region has a first compliancy, said second region has a second compliancy and said third region has a third compliancy.

13. A method according to claim 11, wherein said first region is shared to conform to a share of said ventricular outflow tract when expanded to said first maximum inflated diameter.

* * * * *